(12) United States Patent
Becker et al.

(10) Patent No.: US 11,308,147 B2
(45) Date of Patent: Apr. 19, 2022

(54) METHODS AND SYSTEMS FOR ANALYZING AND REPORTING MEDICAL IMAGES

(71) Applicants: Radlogics, Inc., Los Gatos, CA (US); TEL HASHOMER MEDICAL RESEARCH, INFRASTRUCTURE AND SERVICES LTD., Ramat Gan (IL)

(72) Inventors: Moshe Becker, Los Gatos, CA (US); Robert M. Foley, Palo Alto, CA (US); Eliahu Konen, Tel-Aviv (IL); Arnaldo Mayer, Herzeliya (IL)

(73) Assignees: RADLOGICS, INC., Milpitas, CA (US); TEL HASHOMER MEDICAL RESEARCH, INFRASTRUCTURE AND SERVICES LTD., Ramat Gan (IL)

(*) Notice: Subject to any disclaimer, the term of this patent is extended or adjusted under 35 U.S.C. 154(b) by 132 days.

(21) Appl. No.: 14/201,769

(22) Filed: Mar. 7, 2014

(65) Prior Publication Data

US 2014/0257854 A1 Sep. 11, 2014

Related U.S. Application Data

(63) Continuation of application No. PCT/US2012/054272, filed on Sep. 7, 2012.
(Continued)

(51) Int. Cl.
*G06Q 50/24* (2012.01)
*G16H 15/00* (2018.01)
(Continued)

(52) U.S. Cl.
CPC ............ *G06F 16/50* (2019.01); *G16H 15/00* (2018.01); *G16H 30/20* (2018.01); *G16H 50/20* (2018.01)

(58) Field of Classification Search
CPC .................................. G06Q 50/22–26
See application file for complete search history.

(56) References Cited

U.S. PATENT DOCUMENTS

| | | | | |
|---|---|---|---|---|
| 2007/0238963 A1* | 10/2007 | Kaminaga | ............... | A61B 6/488 600/407 |
| 2008/0040151 A1* | 2/2008 | Moore | ................... | G16H 10/60 705/2 |

(Continued)

FOREIGN PATENT DOCUMENTS

| | | |
|---|---|---|
| KR | 2008/0070767 A | 7/2008 |
| WO | WO 2011/094639 A2 | 1/2011 |

OTHER PUBLICATIONS

The Titi Tudorancea Bulletin, "What does DICOM Study mean? Definition, meaning and sense" as downloaded from https://www.tititudorancea.com/z/dicom_study.htm (Year: 2021).*

(Continued)

*Primary Examiner* — Neal Sereboff
(74) *Attorney, Agent, or Firm* — Jennifer Hayes; Nixon Peabody LLP

(57) ABSTRACT

A method for providing medical diagnostics comprises providing access to one or more platforms capable of distributing one or more applications for implementing a method. The method comprises retrieving, with the aid of a processor, one or more images from an image database or an imaging device. The one or more images can define a set of images. Next, with the aid of a processor, whether each of the images is of medical interest to a reviewing physician is determined. One or more images can then be provided to a display and analysis system for review by a reviewing physician. The one or more images can be provided with an image that is representative of the set of images.

39 Claims, 21 Drawing Sheets

Related U.S. Application Data

(60) Provisional application No. 61/532,540, filed on Sep. 8, 2011, provisional application No. 61/532,519, filed on Sep. 8, 2011, provisional application No. 61/532,514, filed on Sep. 8, 2011, provisional application No. 61/532,515, filed on Sep. 8, 2011.

(51) Int. Cl.
*G16H 30/20* (2018.01)
*G16H 50/20* (2018.01)
*G06F 16/50* (2019.01)

(56) References Cited

U.S. PATENT DOCUMENTS

| | | | | |
|---|---|---|---|---|
| 2008/0097186 A1* | 4/2008 | Biglieri | ............ | G06Q 10/04 600/407 |
| 2008/0118139 A1* | 5/2008 | Huo | ............ | G06T 5/40 382/132 |
| 2008/0215525 A1 | 9/2008 | Kakimoto et al. | | |
| 2008/0253628 A1 | 10/2008 | Matsue et al. | | |
| 2008/0292152 A1* | 11/2008 | Nekrich | ............ | G16H 30/20 382/128 |
| 2009/0022377 A1* | 1/2009 | Matsue | ............ | G16H 30/20 382/128 |
| 2009/0024418 A1* | 1/2009 | Yu | ............ | G06Q 30/04 705/3 |
| 2009/0028403 A1* | 1/2009 | Bar-Aviv | ............ | G16H 50/20 382/128 |
| 2009/0080734 A1* | 3/2009 | Moriya | ............ | G16H 30/40 382/128 |
| 2009/0262894 A1 | 10/2009 | Shukla et al. | | |
| 2012/0283574 A1* | 11/2012 | Park | ............ | G06F 16/5838 600/476 |
| 2013/0039552 A1* | 2/2013 | Becker | ............ | G06K 9/6201 382/128 |

OTHER PUBLICATIONS

U.S. Appl. No. 11/805,532, filed May 23, 2007, Nekrich.
U.S. Appl. No. 12/178,560, filed Jul. 23, 2008, Yu.
U.S. Appl. No. 12/224,652, filed Sep. 3, 2008, Bar-Aviv et al.
International search report and written opinion dated Feb. 27, 2013 for PCT/US2012/054272.

* cited by examiner

METHODS AND SYSTEMS FOR ANALYZING AND REPORTING MEDICAL IMAGES

CROSS-REFERENCE

This application is a continuation of PCT/US2012/054272, filed Sep. 7, 2012, which claims priority to U.S. Provisional Patent Application Ser. No. 61/532,514, filed Sep. 8, 2011, U.S. Provisional Patent Application Ser. No. 61/532,515, filed Sep. 8, 2011, U.S. Provisional Patent Application Ser. No. 61/532,519, filed Sep. 8, 2011, and U.S. Provisional Patent Application Ser. No. 61/532,540, filed Sep. 8, 2011, which applications are entirely incorporated herein by reference.

BACKGROUND

Medical imaging systems, such as computerized tomography ("CT") scanners and magnetic resonance imaging ("MRI") scanners, allow a physician to examine a patient's internal organs and areas of the patient's body that require a thorough examination for medical treatment. In use, a visualizing scanner outputs two-dimensional ("2D") and three-dimensional ("3D") medical images that can include a sequence of computerized cross-sectional images of a certain body organ, which is then interpreted by reviewing physician, such as a specialized radiologist.

Commonly, a patient is referred for a visual scan by a general practitioner or an expert (or specialized) practitioner. A series of 2D and sometimes 3D medical images (or scans) are subsequently obtained. The scan is then forwarded to a reviewing physician (such as a radiologist) who is responsible for the analysis and diagnosis of the scan. Radiologists are typically trained to analyze medical images from various parts of a patient's body, such as medical images of the brain, abdomen, spine, chest, pelvis and joints. After a radiologist (or other reviewing physician) analyzes the medical images, he or she prepares a document ("Radiology Report") that includes radiological findings, and sometimes key images from the scan that best show the findings. The radiology report is then sent back to the referring practitioner.

In most hospitals and radiology centers, the scan is transferred to a picture archiving communication system ("PACS") before being accessed by the radiologists. A PACS is a computer system that acquires, transmits, stores, retrieves, and displays digital images and related subject (or patient) information from a variety of imaging sources and communicates the information over a network. Many hospitals are also equipped with a radiology information system ("RIS")—used by radiology departments to perform patient tracking and scheduling, result reporting and image tracking. Medical images are typically stored in an independent format, such as a Digital Imaging and Communications in Medicine ("DICOM") format. Electronic images and reports are transmitted digitally via PACS, which eliminates the need to manually file, retrieve or transport film jackets. A PACS typically includes four components: the imaging modalities, such as computer axial tomography ("CAT") or CT, MRI, position emission tomography ("PET"), or PET/CT; a secured network for the transmission of patient information; workstations for interpreting and reviewing images; and long and short term archives for the storage and retrieval of images and reports.

There are image retrieval and processing systems and methods available in the art. For example, U.S. patent application Ser. No. 12/178,560 to Yu ("Yu"), entitled "SYSTEMS FOR GENERATING RADIOLOGY REPORTS," which is entirely incorporated herein by reference, provides a method for generating a patient report, comprising presenting an operator with an on screen menu of standardized types of reports and having the operator select a standardized type of report from the on screen menu of standardized types of reports. The operator is presented with an on-screen organ list corresponding to the selected standardized type of report. For each organ, the operator is presented with a menu of standard medical descriptions corresponding to the organ. The operator then determines a medical description corresponding to each organ. Yu further provides outputting a patient report describing the medical description of each organ.

As another example, U.S. patent application Ser. No. 11/805,532 to Nekrich ("Nekrich"), entitled "RADIOLOGY CASE DISTRIBUTION AND SORTING SYSTEMS AND METHODS," which is entirely incorporated herein by reference, provides a system and method for processing an image, including a means for receiving image information, a means for queuing the image information, and a means for receiving profile information for a plurality of image analysts. The system of Nekrich can further include a means for selecting an image analyst from the plurality of image analysts by comparing the image information from the profile information.

As another example, U.S. patent application Ser. No. 12/224,652 to Bar-Aviv et al. ("Bar-Aviv"), entitled "SYSTEM AND METHOD OF AUTOMATIC PRIORITIZATION AND ANALYSIS OF MEDICAL IMAGES," which is entirely incorporated herein by reference, teaches a system for analyzing a source medical image of a body organ. The system of Bar-Aviv comprises an input unit for obtaining the source medical image having three dimensions or more, a feature extraction unit that is designed for obtaining a number of features of the body organ from the source medical image, and a classification unit that is designed for estimating a priority level according to the features.

While current medical image retrieval and processing systems have provided physicians tremendous capabilities in storing and retrieving medical images, there are limitations associated with these systems. For instance, for a typical scan, a hospital may obtain hundreds of images, and a reviewing physician might not have time to review each of the images to determine whether a patient has a particular type of medical condition. In cases in which a hospital scans several patients in a relatively short period of time, the hospital might not have the resources to timely review each patient's (or subject's) medical images to determine whether a physician should further review the image, and whether the patient has a particular type of medical condition.

In addition, modern medical imaging systems can operate much more quickly than older systems, which has led to a decrease in the time it takes to generate a scan. While a shorter scan time could be beneficial for providing rapid patient care, it has resulted in an increase in the amount of data that must be compiled, analyzed and presented to a reviewing physician. Modern medical imaging systems can operate at higher resolutions, resulting in increased number of higher resolution two-dimensional images and/or three-dimensional images (or scans thereof). As the time to generate scans decreases and the number of scans (and images obtained) per patient increases, hospitals without sufficient resources might not be able to review each image and provide patients with medical care in an accurate and efficient manner. Further, while some hospitals might have medical imaging, processing and retrieval systems for handling scans, current systems are not capable of accurately and efficiently prioritizing scans. In addition, current systems do not provide scan reviewing and patient treating physicians with the capability to acquire accurate patient-specific diagnostic information from each of the images or scans.

SUMMARY

This disclosure provides systems and methods for retrieving, analyzing and presenting medical images to a physician or other healthcare provider.

In an aspect of the invention, computer-implemented methods for providing medical diagnostic images and enhanced report capabilities are provided.

In an embodiment, a computer-implemented method for providing medical diagnostic images comprises using a computer system to retrieve one or more images from an image database or an imaging device (e.g., imaging modality), the one or more images defining a set of images; using the computer system to determine whether each of the images is of medical interest to a reviewing physician; using the computer system to determine whether one or more of the images is representative of the set of images; and providing the one or more images to a display and analysis system for review by a reviewing physician, wherein the one or more images are provided with an image that is representative of the set of images.

In another embodiment, a computer-implemented method for providing enhanced report capabilities for medical diagnostic images comprises retrieving one or more images from an image database or an imaging device, the one or more images defining a set of images; determining whether each of the images is of medical interest to a reviewing physician; determining whether one or more of the images is representative of the set of images; providing the one or more images to a display and analysis system for review by a reviewing physician; and providing one or more text blocks associated with items determined to be of medical interest, the one or more text blocks for being mixed, matched and edited by a reviewing physician to create a report.

In another aspect of the invention, a system for visualizing and reporting patient-specific (or subject-specific) medical information comprises an imaging modality for retrieving medical diagnostic images from a patient (or subject); a reviewing system for displaying medical images to a reviewing physician; a prioritization visualization and reporting system in communication with the imaging modality and the reviewing system, wherein the prioritization visualization and reporting system is for retrieving one or more images from the imaging modality, the one or more images defining a set of images, determining whether each of the images is of medical interest to a reviewing physician, determining whether one or more of the images is representative of the set of images and providing the one or more images to the reviewing system, wherein the one or more images are provided with an image that is representative of the set of images.

In another aspect, a method for providing medical diagnostic images comprises retrieving, using a processor, one or more images from an image database or an imaging device, the one or more images defining a set of images; selecting one or more images from the set of images based on diagnostic data stored within a memory; generating a report including the one or more selected images and providing the report to a reviewing physician; receiving one or more modifications to the report from the reviewing physician; and updating the diagnostic data based on the modification.

In an embodiment, a method for providing medical diagnostic images comprises retrieving, using a processor, one or more images from an image database or an imaging device, the one or more images defining a set of images; selecting one or more images from the set of images based on diagnostic data stored within a memory; generating a report including the one or more selected images and providing the report to a reviewing physician; receiving patient outcome information relating to patient responsiveness to treatment; and updating the diagnostic data based on the patient outcome information.

In another aspect, a system for providing medical diagnostic images comprises a database operatively coupled to an imaging device, the database configured to store one or more images from the imaging device, the one or more images defining a set of images; and a processor configured to: generate a report from one or more images selected from the set of images and provide the report for review by a reviewing physician, wherein said one or more images are selected based on diagnostic data stored in the database; receive one or more modifications to the report from the reviewing physician; and update the diagnostic data based on the one or more modifications.

In another aspect, a method for providing medical diagnostic images comprises retrieving, using a processor, one or more images from an image database or an imaging device, the one or more images defining a set of images; retrieving, one or more boundary parameters from a memory; determining, using a processor, whether each of the images is falls within the boundary parameters; and providing one or more alert for an urgent medical condition if one or more of the images falls within the boundary parameters.

In another aspect, a system for providing medical diagnostic images comprises an imaging modality for retrieving medical diagnostic images from a patient; a database comprising one or more boundary parameters; a processor configured to compare the retrieved images with the one or more boundary parameters; and an alert system in communication with the imaging modality and database configured to provide one or more alert for an urgent medical condition if one or more of the images falls within the boundary parameters.

In another aspect, a method for providing patient medical diagnostic images comprises retrieving, using a processor, one or more images associated with a patient from an image database or an imaging device, the one or more images defining a set of images; retrieving, historical data of said patient from a memory; comparing, using a processor, the one or more images with the historical data; and providing the one or more images and the historical data to a reviewing physician In another aspect, a system for providing medical diagnostic images comprises an imaging modality for retrieving medical diagnostic images from a patient; a database comprising historical data of said patient; a processor configured to compare the retrieved images with the historical data of said patient; and a prioritizing, visualization and reporting system in communication with the imaging modality and the database configured to provide the images and the historical data to a reviewing physician.

In another aspect, a method for providing medical diagnostics comprises providing access to one or more platforms capable of distributing one or more applications for implementing a method, the method comprising: retrieving, using a processor, one or more images from an image database or an imaging device, the one or more images defining a set of images; determining, using a processor, whether each of the images is of medical interest to a reviewing physician; and providing one or more images to a display and analysis system for review by a reviewing physician, wherein the one or more images are provided with an image that is representative of the set of images.

In another aspect, a system for providing medical diagnostics comprises one or more platforms capable of distributing one or more applications for implementing a method, the method comprising: retrieving, using a processor, one or more images from an image database or an imaging device, the one or more images defining a set of images; determining, using a processor, whether each of the images is of medical interest to a reviewing physician; and providing one or more images to a display and analysis system for review by a reviewing physician, wherein the one or more images are provided with an image that is representative of the set of images. The system further comprises an interface configured to receive one or more user input related to the distribution of the one or more applications.

In another aspect, a method for providing medical diagnostic images comprises (a) retrieving, with the aid of a processor, one or more images from an image database or an imaging device, the one or more images defining a set of images; (b) selecting, with the aid of a processor, one or more images from the set of images based on diagnostic data stored within a memory; (c) generating a report including the one or more selected images and providing the report to a reviewing physician; (d) receiving one or more modifications to the report from the reviewing physician; and (e) updating the diagnostic data based on the one or more modifications.

In another aspect, a method for providing medical diagnostic images comprises (a) retrieving, with the aid of a processor, one or more images from an image database or an imaging device, the one or more images defining a set of images; (b) selecting one or more images from the set of images based on diagnostic data stored within a memory; (c) generating a report including the one or more selected images; (d) providing the report to a reviewing physician; (e) receiving subject outcome information relating to subject responsiveness to treatment; and (f) updating the diagnostic data based on the subject outcome information.

In another aspect, a system for providing medical diagnostic images comprises (a) a database operatively coupled to an imaging device, the database configured to store one or more images from the imaging device, the one or more images defining a set of images; and (b) a processor coupled to said database, wherein said processor is programmed to: (i) generate a report from one or more images selected from the set of images and provide the report for review by a reviewing physician, wherein said one or more images are selected based on diagnostic data stored in the database; (ii) receive one or more modifications to the report from the reviewing physician; and (iii) update the diagnostic data based on the one or more modifications.

In another aspect, a method for providing medical diagnostic images comprises (a) retrieving, with the aid of a processor, one or more images from an image database or an imaging device, the one or more images defining a set of images; (b) retrieving, one or more boundary parameters from a memory location coupled to said processor; (c) determining whether each of the images falls within said boundary parameters; and (d) providing one or more alerts for an urgent medical condition if, based on said determining of (c), a given image among said one or more of images falls within the boundary parameters.

In another aspect, a system for providing medical diagnostic images comprises (a) an imaging modality for retrieving medical diagnostic images from a subject; (b) a database comprising one or more boundary parameters; (c) a processor coupled to said imaging modality and said database, wherein said processor is programmed to compare images retrieved from said imaging modality with the one or more boundary parameters; and (d) an alert system in communication with the imaging modality and said database, wherein said alert system is configured to provide one or more alerts for an urgent medical condition if one or more of said images fall within the boundary parameters.

In another aspect, a method for providing subject medical diagnostic images comprises (a) retrieving, with the aid of processor, one or more images associated with a subject from an image database or an imaging device, the one or more images defining a set of images; (b) retrieving, historical data of said subject from a memory location; (c) comparing, with the aid of a processor, the one or more images with the historical data; and (d) providing the one or more images and the historical data to a reviewing physician.

In another aspect, a system for providing medical diagnostic images comprises (a) an imaging modality for retrieving medical diagnostic images from a subject; (b) a database comprising historical data of said subject; (c) a processor programmed to compare the retrieved images with the historical data of said subject; and (d) a prioritizing, visualization and reporting system in communication with the imaging modality and the database, wherein said prioritizing, visualization and reporting system provides the images and the historical data to a reviewing physician.

In another aspect, a method for providing medical diagnostics comprises (a) providing access to one or more platforms programmed to distribute one or more applications which, upon execution by a processor, implement a method, the method comprising: (i) retrieving, with the aid of a processor, one or more images from an image database or an imaging device, the one or more images defining a set of images; (ii) determining, with the aid of a processor, whether each of the images is of medical interest to a reviewing physician; and (iii) providing one or more images to a display and analysis system for review by a reviewing physician, wherein the one or more images are provided with an image that is representative of the set of images.

In another aspect, a system for providing medical diagnostics comprises (a) one or more platforms programmed to distribute one or more applications which, upon execution by a processor, implement a method, the method comprising: (i) retrieving, with the aid of a processor, one or more images from an image database or an imaging device, the one or more images defining a set of images; (ii) determining, with the aid of a processor, whether each of the images is of medical interest to a reviewing physician; and (iii) providing one or more images to a display and analysis system for review by a reviewing physician, wherein the one or more images are provided with an image that is representative of the set of images. The system further comprises (b) a user interface adapted to receive one or more user inputs related to the distribution of the one or more applications.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the invention will be obtained by reference to the following detailed description that sets forth illustrative embodiments, in which the principles of the invention are utilized, and the accompanying drawings (also "FIG." herein), of which:

FIG. 14b shows an exemplary process for an optional continuation of the process of FIG. 14a;

DETAILED DESCRIPTION

Figure 1:
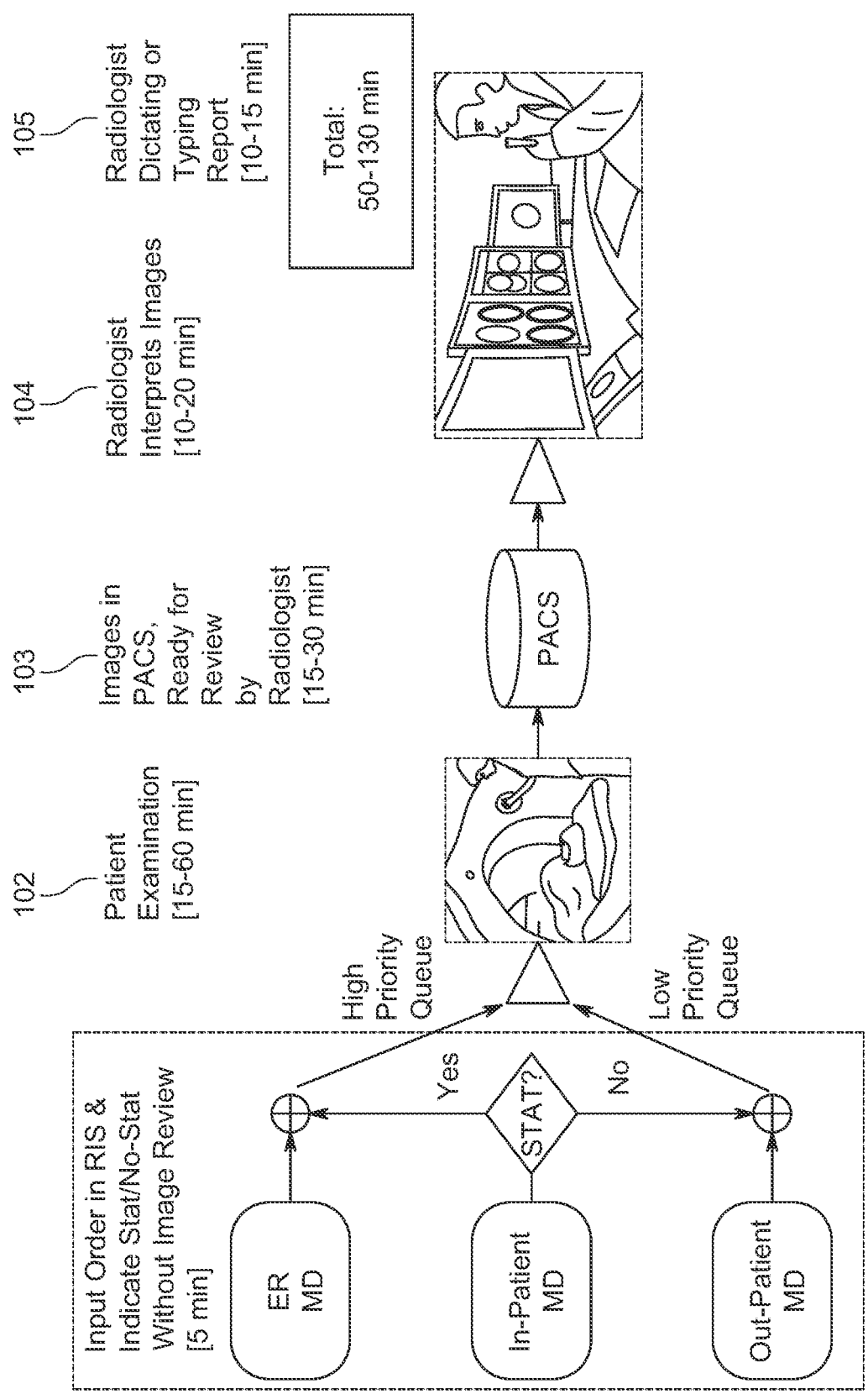
FIG. 1 shows a medical imaging workflow with a timeline, in accordance with an exemplary embodiment of the current art.

While various embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

In view of the various limitations of current medical image retrieval and processing systems, there is recognized herein a need for improved imaging, analysis, prioritization and reporting systems. In particular, there is recognized herein a need for methods and systems for accurately and efficiently analyzing and prioritizing medical images, such as images acquired from CT scans and MRIs, to provide better patient (or subject) risk management.

Some embodiments provide a system and method for using a computer to retrieve images from a database and to determine whether each of the images is of medical interest to a reviewing physician. In some cases, system and method are provided for using the computer to determine which one (or more) of the images is representative of the full set of images and providing that representative image or images to a display and analysis system for review by a reviewing physician, so the patient outcome may be tracked by continuously following the initial findings and the responsiveness to treatment, and also by tracking the clinical diagnosis and comparing that with initial radiological findings and then following up in clinical treatment up to full resolution of the problem to determine whether the initial findings were supported or not, and if not, what the discrepancies are. By tracking patient outcome the diagnostics can be further enhanced and refined over time, thus improving the results.

Some embodiments provide a system and method for machine learning at two levels, a first level and a second level. On the first level, the system looks at the final report by a radiologist and compares it to the system's automatically generated preliminary report, adjusting/refining algorithms to more closely match the radiologist's report. This approach involves automatic processing of many cases and using analytics/statistical processing of vast amounts of data to improve diagnostic algorithms and hence patients outcome. The second level requires tracking the patient outcomes beyond the radiological report, e.g., reports by referring physician, other, to better understand patient's real condition and automatically refining algorithms to better match real patient condition.

Some embodiments provide a system and method to alert physicians to potentially serious findings in as close as possible to real time. Some embodiments provide a system and method for supporting comparisons between current and historical data, both to the individual and to peer groups.

In some cases, a user may need to download additional modules for the system and method disclosed throughout herein. In current practice, a user may download additional modules and features for an existing system from an application ("app") store.

Some embodiments provide a system and method in an app store environment, including an application management module and the actual store itself from which users may download, evaluate, and purchase apps.

Some applications may be downloaded that are for research use only, because these applications are not approved for medical use by a regulatory body (e.g., the United States Food and Drug Administration, "FDA") charged with regulating the use and/or distribution of the applications. These applications may be activated only when the system and method disclosed herein throughout is in a "research only" mode. During said research mode, no real patient data may be used for clinical or actual medical purposes; the patient (or subject) data may be used solely for research and testing purposes. When the system is in "clinical" mode, all the unapproved applications must be suspended. In some cases, the system may have various approval modes, such as a different approval mode for each different regulatory agency.

For example, certain products and plug-ins may be approved in Europe but not approved in the United States, or vice versa. In a given system, multiple approval modes may be available, and a user, such as a physician, may switch between modes. In a system configured with multiple approval modes, one mode is designated the default mode, usually determined by the system location (e.g., Europe or the U.S.) and purpose. If the system is not in its default mode, an alert is displayed on screen, such as, for example, a red blinking frame around the screen display as a reminder that the system is in a non-default mode. For example, if the system is being used in the U.S. in a mode other than the default FDA-approved mode, a non-default mode indicator means some of the modules in use are not FDA-approved. Any files and documents created in a non-default mode may have a clear overlay imprint showing, for example, "Not FDA approved," which may indicate that the files and documents have not been approved for use by the regulatory body (e.g., FDA) whose approval is required in the default mode when the system is in use.

The invention provides methods and systems for analyzing and prioritizing medical images, and for reporting medical findings. For example, an analysis of medical images according to some aspects of the system and methods disclosed herein may be used to identify critical medical conditions, and, based on this analysis, the system and method may further be used to organize a work list for a reviewing physician based on the severity of the medical findings and to then create a text document that lists the medical findings in the analyzed medical images. For example, a database may be created, showing a "normalized" version of each possible aspect of a region. Accordingly, deviations above a certain threshold may be used to flag a certain image. Furthermore, in some areas, just the appearance of an unexpected presence (for example, a liquid in the pleural space) maybe used to flag an image or a series of images. It is clear that many variations can be done without changing the spirit of the invention. Various aspects of the invention described herein may be applied to any of the particular applications set forth below or for any other types of displays, or radiological data management applications. The invention may be applied as a standalone system or method, or as part of an integrated software package, such as a medical and/or laboratory data management package or application, or as part of an integrated picture archiving communication systems ("PACS") solution. It shall be understood that different aspects of the invention can be appreciated individually, collectively, or in combination with each other.

Current medical imaging, processing and retrieval systems are incapable of providing sufficient patient risk management. This is due at least in part to the lack of case prioritization. In addition, hospitals may not have the resources to review and analyze each medical image in a set of medical images in a timely manner, and current PACS do not provide physicians the resources to efficiently and accurately analyze, prioritize, and report findings in medical images.

In some embodiments of the invention, methods and systems are provided for efficiently and accurately interpreting medical images, acquiring quantitative measurements for each of the medical images, and providing the reviewing physicians the capability to generate medical reports. Methods and systems of embodiments of the invention can provide hospitals with the capability to streamline their medical image processing, which advantageously reduces the time and resources necessary to review each scan (e.g., CT/CAT, MRI, PET/CT) associated with a subject (e.g., patient), and provide physicians accurate data necessary to provide adequate medical care.

In some embodiments of the invention, methods and systems are provided for analyzing medical images (e.g., CT scans of the chest, abdomen, and head). Methods and systems of embodiments of the invention improve the quality of patient care by automatically prioritizing cases prior to review by a reviewing physician or specialist (e.g., radiologist) based on pathological findings. In various embodiments, methods and systems for analyzing and prioritizing medical images generate preliminary reports, which are available to reviewing physicians as they open cases for review. This advantageously reduces the time it takes a radiologist to prepare a final report. The report can include additional information, such as quantified measurements (e.g., cross-sectional areas, volumes) automatically extracted, generated, or calculated from the data. Methods and systems of embodiments of the invention can seamlessly integrate into an existing radiological workflow.

With reference to FIG. 1, a typical medical imaging workflow as currently used is shown. Approximate lengths of time associated with each step in the workflow are also indicated in the figure. Such times are provided by way of example only. It will be appreciated that other times are possible.

Initially, in step 101, a patient is admitted to a hospital or other healthcare provider for treatment or a routine checkup. For example, the patient may be admitted through the emergency room ("ER"), the in-patient unit, or the out-patient unit of a healthcare provider. An admitting physician or nurse conducts a preliminary examination of the patient to determine whether the patient's condition warrants immediate medical attention (i.e., "Stat" or "No-Stat"). For instance, the admitting physician can determine whether the patient's condition is of high or low priority. The admitting physician or nurse may indicate the patient's status (e.g., high priority, low priority) in a patient tracking system, such as the patient tracking feature of a radiology information system ("RIS"). The admitting physician or nurse can also indicate "Stat" or "Non-Stat" (or "No-Stat"). Cases indicated as "Stat" may be placed in a high priority queue while cases indicated as "No-Stat" can be placed in a low priority queue.

With continued reference to FIG. 1, in a patient examination step 102, medical images (e.g., CAT/CT scan, MRI, PET/CT scan) are obtained from a patient. Medical images may be obtained using a variety of methods. For example, a three-dimensional image (with 2-D cross-sections) of a particular region of a patient's body may be obtained using a CT scanner. As another example, a three-dimensional image may be obtained using an MRI. Such three-dimensional image may have two-dimensional cross-sectional images. Alternatively, multiple images may be provided, whether they originate from a three-dimensional image or not. Medical images (or scans) thus obtained are stored in a PACS. The PACS makes these images available for review by a reviewing physician or specialist (e.g., radiologist).

Next, in step 103, a radiologist retrieves and interprets the images obtained during the patient examination step. The radiologist reviews all of the images in a case in step 104.

In the next step 105, the radiologist prepares a report having the radiologist's analysis of the patient's medical images. The radiologist might dictate (or type) a report comprising the radiologist's diagnosis of the patient's condition. The radiologist may add to the report images taken from the case that show visual representation of the diagnosis ("Key Images"). The radiologist can then make the report available for review by a referring physician.

Picture Analysis Prioritization Visualization and Reporting System

In an aspect of the invention, a computer system is provided for improving the efficiency and accuracy of a workflow process. In some embodiments of the invention, the computer system, which, for example, could be a standard personal computer with a standard CPU, memory and storage, is an enhanced picture archiving communication system, or an add-on subsystem to an existing PACS and/or RIS. In some embodiments of the invention, the computer system can be configured to analyze and prioritize images and patient cases. The computer system can be referred to as a picture analysis prioritization visualization and reporting system (also "PAPVR system" herein). The computer system can automatically retrieve medical images from an imaging modality (e.g., CAT/CT scanner, MRI, PET/CT scanner) or a database in which medical images are stored, or a PACS, automatically analyze the medical images, and provide the medical images and the results of the analysis for review by a reviewing or referring physician, or a specialist, such as a radiologist.

Figure 2:
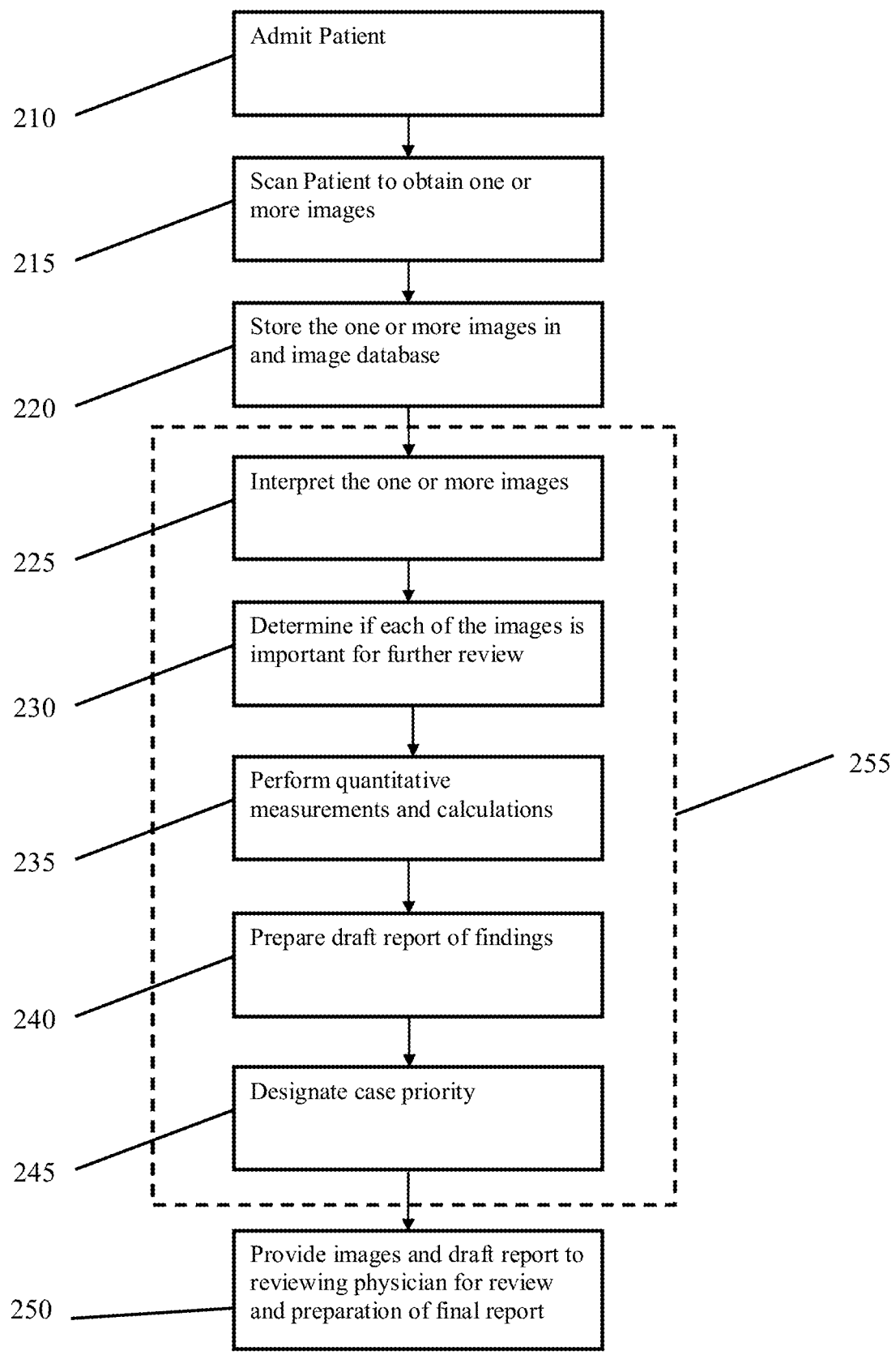
FIG. 2 shows an examination workflow, in accordance with an embodiment of the invention.

With reference to FIG. 2, an examination workflow is illustrated, in accordance with an embodiment of the invention. In a first step 210, a patient is admitted for treatment or a routine checkup. An admitting physician or nurse can determine whether the patient's condition is of high priority or low priority. Next, in step 215 a predetermined region of the patient's body is scanned. In an embodiment, a predetermined region of the patient's body is imaged using CT (or CAT) scan. In another embodiment, a predetermined region of the patient's body can be imaged using MRI, PET scan, or PET/CT scan. Scanning the patient can provide one or more images (e.g., 2-D or 3-D images) of a predetermined region of the patient's body. Next, in step 220 the one or more images (or set of images) are stored in an image database. In an embodiment, the image database can be a subsystem of a PACS. In another embodiment, the image database can be a standalone computer system. In such a case, the standalone computer system can be in communication with a PACS.

With continued reference to FIG. 2, in step 225, the one or more images are analyzed by a PAPVR system (or enhanced PACS), in accordance with an embodiment of the invention. In an embodiment, a subset of the one or more images is analyzed and interpreted by the PAPVR system. Next, in step 230, the PAPVR system reviews the one or more images to determine whether the one or more images would be of interest (e.g., Key Images) to a reviewing or referring physician. This can entail determining whether the one or more images show any abnormalities with respect to the patient's condition, for example, free pleural air (pneumothorax) or fluid, aortic dissection, intracranial hemorrhage, liver metastases etc. These various conditions, for example, can be determined using comparable images, as well as comparing them to normalized images as described throughout herein. In an embodiment, the PAPVR system can determine whether each or a subset of the one or more images is important for further review by a reviewing or referring physician. In some cases, further the system may perform additional analysis, including but not limited to providing quantitative measurements, as well as, in some cases, the indication of the localization (for example with an added color overlay that can be turned off for better viewing, or other suitable methods) where the measurement has been performed. This localization is more specific than a keyframe as it may be a small region inside a key frame. For example, When we detect blood in the pleural effusion (hemothorax), we can highlight the areas where blood was detected into the pleural effusion. This can save time in some cases since if blood is detected correctly somewhere in the pleural effusion and the radiologist is brought automatically to that place for verification, the radiologist can diagnose the hemothorax without further measuring liquid intensity in other slices.

Next, in step 235, the PAPVR system can perform quantitative measurements and calculations (e.g., distances, cross-sectional areas, volumes), that is relevant to the patient's condition, for example, measuring the volume of air in a pneumothorax by doing image analysis as described herein. Next, in step 240, the PAPVR system can create a draft report that includes the findings, calculations and Key Images. Next, in step 245, the PAPVR system can designate case priority. Next, in step 250, the PAPVR system can provide the one or more images and the draft report for review and preparation of the final report by a reviewing or referring physician. In an embodiment, the one or more images can be provided with the PAPVR system's interpretation of the one or more images. The steps 225, 230, 235, 240 and 245 can be collectively referred to as step 255.

Further, in some cases, the system could be automatically comparing the present study with a previous similar study obtained on the same patient in the past; in these cases the invention can compare findings and quantify changes such as increased pleural fluid or increased dilatation of an aortic aneurysm which has significant clinical implications.

In an aspect of the invention, methods for retrieving and processing medical diagnostic images are provided. The methods comprise using a computer system, such as an enhanced picture archiving communication system (also "picture archiving communication and analysis system" herein), to retrieve one or more images (e.g., two-dimensional images from a three-dimensional scan) from an image database or directly from an imaging device (e.g., imaging modality). In an embodiment, the one or more images define a set of images. Next, the computer system determines whether each of the images is of medical interest to a reviewing physician, for example, by identifying the image that shows the point in which the aorta is seen at its widest diameter, or, for example, by analyzing that specific aspect in a series of volumetric images and calculating the value, and then flagging the one with the largest numeric value, either by dimension, area or any other suitable measure. In an embodiment, this can include the computer system comparing each of the images to images from patients with known medical conditions. Next, the computer system determines whether one or more of the images is representative of the set of images and designates them as Key Images. The computer system then provides the one or more images to a display and analysis system for review by a reviewing physician. In addition, using the above image comparisons, the computer system can detect whether a patient suffers from a particular ailment, and provide a reviewing physician quantitative information (e.g., distances, cross-sectional areas, volumes), that is relevant to the patient's condition.

In an aspect of the invention, a PAPVR system is provided for automatically retrieving, reviewing and analyzing one or more medical images acquired from an imaging modality. In some embodiments, the PAPVR system can analyze and interpret each or a subset of one or more images acquired by an examination system, such as an imaging modality (e.g., CAT/CT scan, MRI, PET/CT scan). In some case, the PAPVR system can be referred to as an enhanced or improved PACS. The PAPVR system of preferable embodiments can automatically perform step 255 of FIG. 2.

In preferable embodiments of the invention, the PAPVR system is configured to automatically detect and quantify various physiological features or abnormalities, for example, by using image processing algorithms that identify the pneumothorax condition, and other image processing algorithms that can segment the area of the pneumothorax and calculate its volume, as discussed exemplarily throughout this document. By automatically detecting various physiological features or abnormalities, the PAPVR system of embodiments of the invention can advantageously reduce the time and resources required to review images provided from an imaging modality (e.g., CT scan, MRI, PET/CT). This increases the accuracy of detection and quantification, and provides for improved patient care and more efficient workflow. PAPVR systems of embodiments of the invention advantageously enable healthcare providers to provide patients with accurate and rapid patient care.

Figure 3:
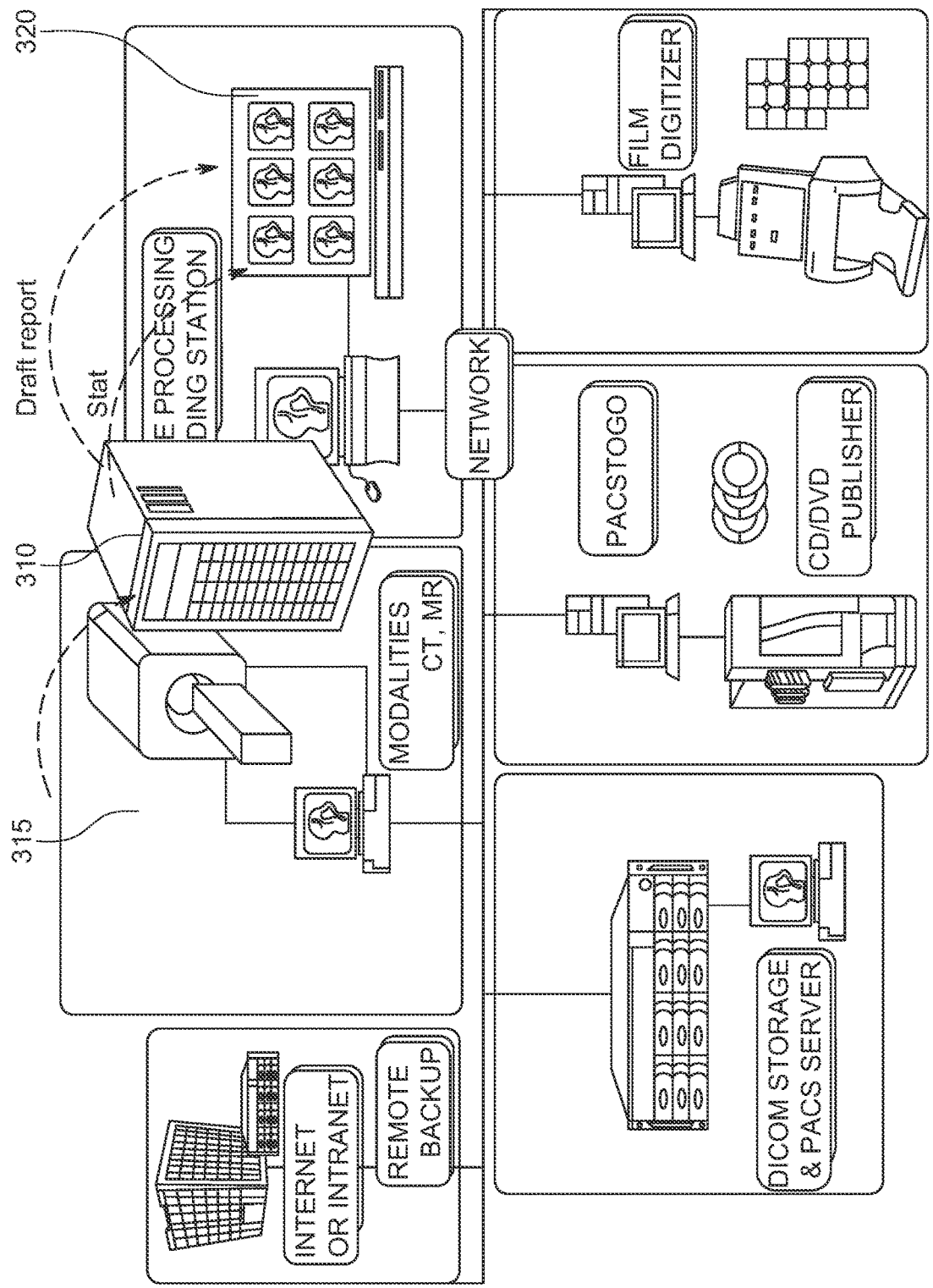
FIG. 3 shows a picture analysis prioritization visualization and reporting ("PAPVR") system as part of a workflow system, in accordance with an embodiment of the invention.

With reference to FIG. 3, in an embodiment of the invention, a PAPVR system 310 configured to retrieve, analyze and interpret one or more images provided by an examination system is illustrated, in accordance with an embodiment of the invention. The PAPVR system 310 can include tangible, non-transitory computer readable media. The PAPVR system 310 can be part of a healthcare provider's workflow. In an embodiment, the PAPVR system can automatically perform step 255 of FIG. 2. The PAPVR system 310 can retrieve images from a storage unit that can be part of the PAPVR system 310, or from a separate PACS system 325, and prepare the images for review. The PAPVR system 310 can be in communication with other components or computer systems (also "systems" herein) of a healthcare provider. In an embodiment, the PAPVR system 310 can be physically situated at the location of a healthcare provider (i.e., the PAPVR system can be on-site). In such a case, the PAPVR system can communicate with other components or systems of the healthcare provider via the healthcare provider's network, such as an intranet. In another embodiment, the PAPVR system 310 can be an off-site system that communicates with other components of a healthcare provider via the Internet or World Wide Web.

With continued reference to FIG. 3, the PAPVR system 310 is configured to retrieve one or more images from an examination system 315 or a PACS 325; analyze and interpret (also referred to as "process" herein) some or all of the one or more images; and provide the one or more images for review by a referring or treating physician. In an embodiment, following processing, the PAPVR system 310 can provide the images to a reviewing system 320 configured to display the images to a physician. In an embodiment, the PAPVR system 310 can analyze and interprets each cross-section of a three-dimensional scan of a particular region of a patient's body. The PAPVR system can contain, receive, or utilize computer readable media, which may contain instructions, logic, data, or code that may be stored in persistent or temporary memory of a computer, or may somehow affect or initiate action by the PAPVR systems, or any computers or servers contained therein. Any steps or analysis described herein may be performed by utilizing such computer readable media.

In some embodiments, the PAPVR system 310 can automatically detect various physiological features, again, for example, by using image processing algorithms that identify the pneumothorax condition, and another image processing algorithm that can segment the area of the pneumothorax and calculate its volume. For example, the PAPVR system can automatically detect air and/or liquid pockets and quantify (or calculate) the volume of the air and/or liquid pockets. The PAPVR system can also quantify cross-sectional areas and distances. In some embodiments, the PAPVR system can detect bones and organs, and quantify the cross-sectional areas and/or volumes of the bones and organs.

In some embodiments, the PAPVR system 310 can provide additional data with each of the one or more images. The PAPVR system 310 can provide the additional data for review by a reviewing or referring physician (using the reviewing system 320, for example). The additional data can include distances (e.g., distances between features) cross-sectional areas, gas (e.g., air) volumes, liquid (e.g., blood) volumes, blood vessel cross-sectional measurements, location and number of bone fractures, and shift in the position of body organs such as the mediastinum in tension pneumothorax. In an embodiment, when a physician accesses each of the one or more images, the additional data is made accessible to the physician. In an embodiment, when the physician views a two-dimensional cross-sectional image of a three-dimensional image, the additional data is provided with each two-dimensional cross-sectional image. In some embodiments, additional data may be provided with each image by way of metadata associated with each image.

With continued reference to FIG. 3, the PAPVR system 310 can be in communication with other systems or components associated with the healthcare provider's workflow system. In some embodiments, the PAPVR system 310 can be in communication with one or more of an imaging modality (e.g., CAT/CT scan, MRI, PET/CT scan) remote backup system, a DICOM storage and PACS server 325, a PACStoGO system, a CD/DVD publishing system and a film digitizer. The PAPVR system 310 can be in communication with other workflow systems and/or components via an intranet, the Internet (e.g., wired or wireless web), or other mode of communication, such as Bluetooth. In some embodiments, the PAPVR system can be configured to interact manually or automatically with one or more systems or components associated with a workflow system.

Figure 4:
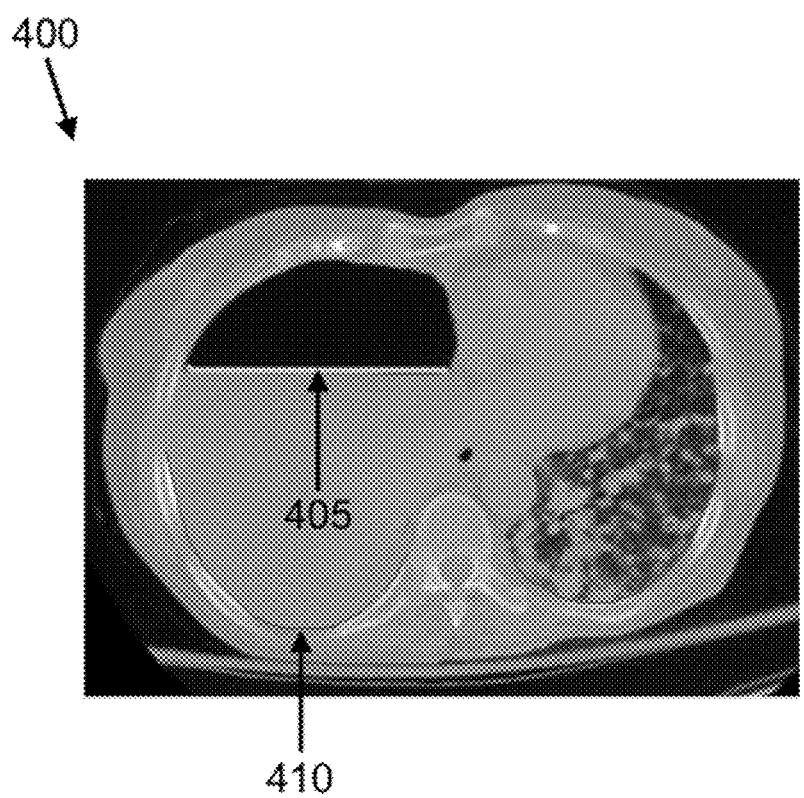
FIG. 4 shows a CT scan of a patient's pleural cavity, in accordance with an embodiment of the invention.

FIG. 4 shows one image of a CT scan 400 processed by a PAPVR system of embodiments of the invention. The image 400 is a two-dimensional cross-sectional image of a patient's pleural cavity. The image 400 is one example of an image among many images that can be provided from a CT scan. The CT scan shows free pleural effusion, free pleural air and mediastinal shift (=tension hydropneumothorax) 405 and the patient's rib cage 410. In some embodiments, the PAPVR system is configured to automatically detect a pleural effusion and quantify the volume of free liquid and free air in the patient's pleural cavity and identify the mediastinal shift which suggest a medical emergency. In an embodiment, the PAPVR system can also automatically detect the presence of an air volume or space (e.g., pneumothorax) and quantify the volume. In some embodiments, the PAPVR system can automatically detect and quantify various physiological features or abnormalities, such as, e.g., pneumothorax, tension pneumothorax, pleural effusion, ascending and descending aortic caliber and aortic dissections.

Key Image

In an aspect of the invention, a PAPVR system can be configured to provide a radiologist or other reviewing physician with one or more images, Key Images, that are representative of a set of images and/or representative of the patient's condition.

Figure 5:
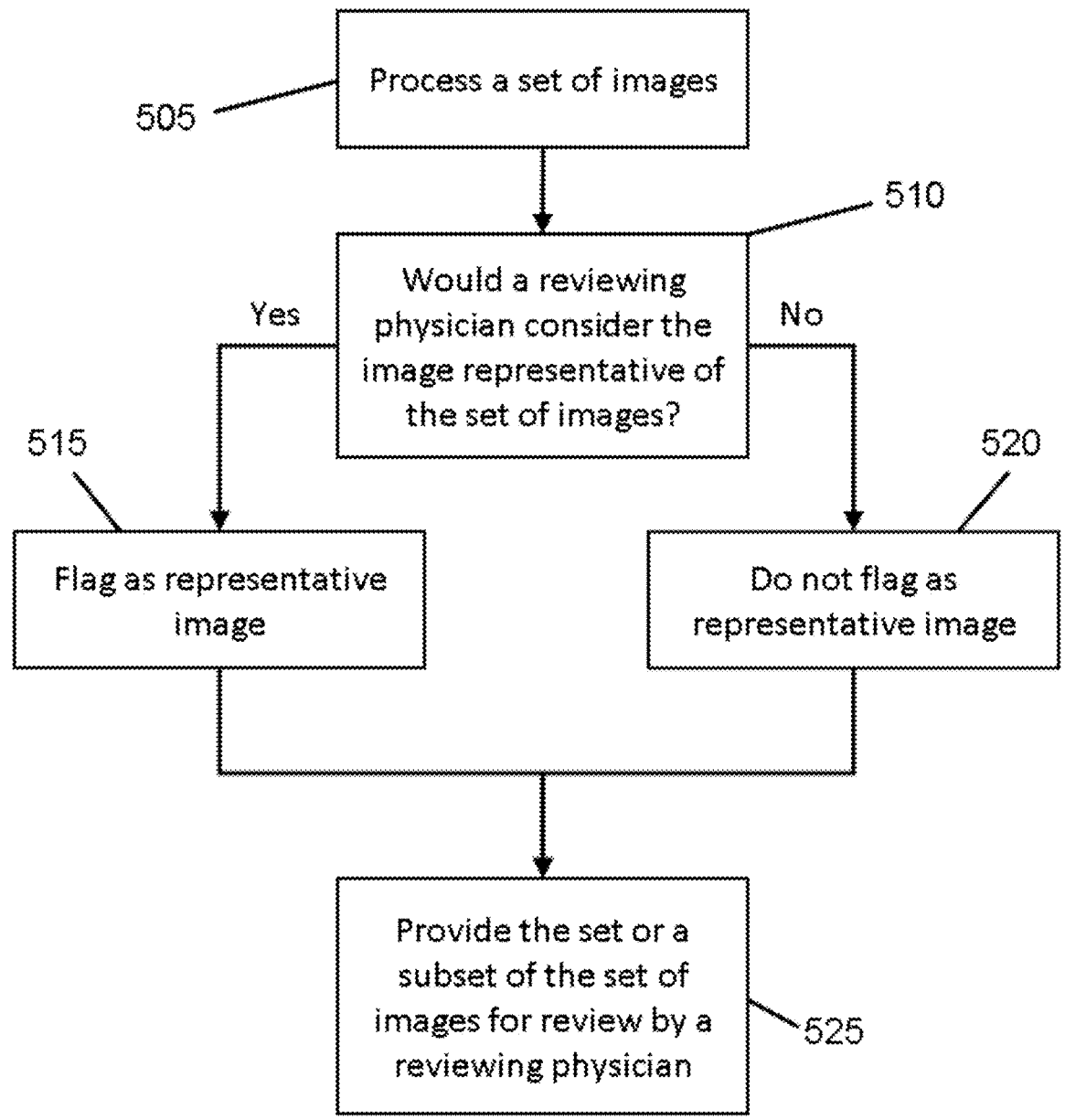
FIG. 5 shows steps taken in flagging an image as a representative image, in accordance with an embodiment of the invention.

With reference to FIG. 5, in an embodiment, a PAPVR system can automatically identify one or more images as Key Images, based on, for example, the image that shows the aorta at its widest. In an embodiment, a Key Image is an image that is representative of a set of images. In another embodiment, a Key Image is representative of the patient's condition. In such a case, the Key Image can best capture the patient's condition. In some cases, the Key Image can accurately define a set of images. For instance, if a patient's CT scan shows a pleural effusion, the Key Image can be the image (e.g., two-dimensional cross-sectional image) determined by the PAPVR system to clearly and accurately show the pleural effusion. In some embodiments, when the PAPVR system provides one or more images and data for review by a reviewing (such as a radiologist) or referring physician, the Key Image can be the first image the reviewing physician observes. In other embodiments, the Key Images provided by the PAPVR system can be the images used by the reviewing physician in the final report prepared for the referring physician. For example, a Key Image can be found by comparing tissue density of certain sections with average examples (i.e., liquids have a different density than "normal tissue") or structural abnormalities, such as "speckles" of another density, which could indicate for example tumors, or fracture lines in a bone, etc.

With continued reference to FIG. 5, in a first step 505, the PAPVR system retrieves an image (e.g., two-dimensional cross-section of a three-dimensional image or scan) for processing. Next, in step 510, the PAPVR system determines whether a reviewing physician would consider the image representative of the set of images. If the image is determined to be representative of the set of images, in step 515 the image is flagged as a "Key Image." If the image is determined to not be representative of the set of images, in step 520 the image is not flagged as a "Key Image." Next, in step 525, the set of images or a subset of the set of images is provided to a reviewing (or treating) physician for review. In an alternative embodiment, if an image is not found to be representative, the PAPVR system can skip step 515 and proceed directly to step 525.

Image Prioritization

In an aspect of the invention, a PAPVR system can automatically prioritize an image. Image prioritization can advantageously reduce time and resources required by a reviewing or treating physician to make an accurate diagnosis. In some embodiments, the PAPVR system can flag some images as having a higher priority relative to other images, and a physician or radiologist can review only those images, thus saving considerable time in analyzing images associated with a particular scan.

A PAPVR system of embodiments of the invention can automatically prioritize an image. In an embodiment, the PAPVR system can be configured to flag an image as having a "high priority" or a "low priority." In other embodiments, the PAPVR system can flag an image as having high, medium or low priority. In an embodiment, the PAPVR system can categorize an image among a predetermined number of categories. For example, one, two, three, four, five, six, seven, eight, or more categories may be utilized. In still other embodiments, the PAPVR system can assign a numerical value (e.g., 1-10, 1-100, 1-1000, 1-10,000) to an image that is indicative of the priority of the image. For example, a high priority image can be assigned a numerical value of 1, while a low priority image can be assigned a numerical value of 100. In some embodiments, the user can specify how an image is to be prioritized. For example, the user can specify that images are to be prioritized as high, medium, or low priority.

In some embodiments, a user (e.g., a reviewing/referring physician, radiologist) can request that the PAPVR system only provide images having a priority that is above a minimum (or cut-off) priority. For example, the user can request that the system provide only high priority images for review. As another example, the user can request that the PAPVR system provide images having a priority numerical value above a certain value or within a certain range. In some embodiments, the user can specify the minimum (cut-off) priority.

Figure 6:
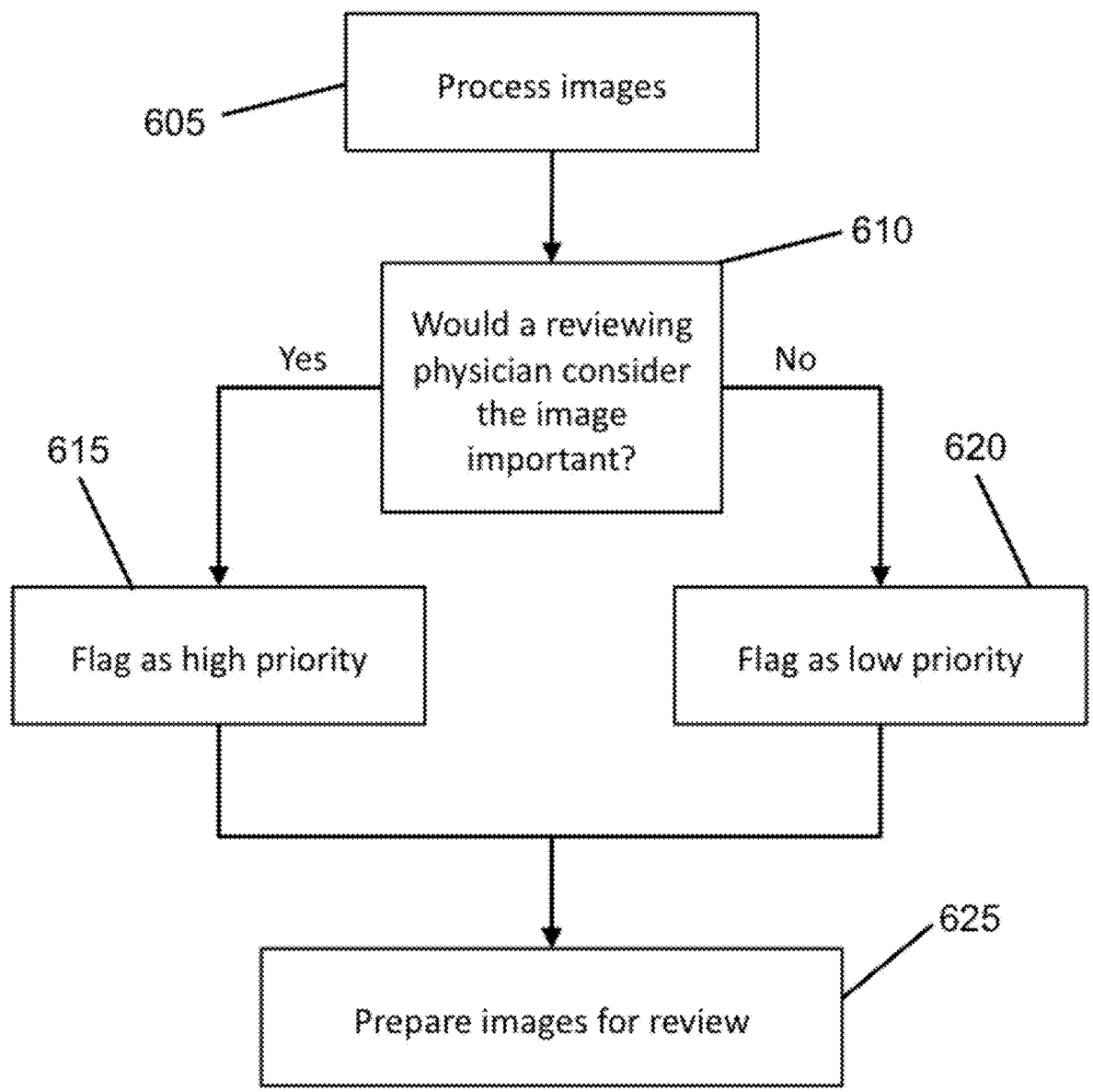
FIG. 6 shows a series of steps for prioritizing medical images, in accordance with an embodiment of the invention.

With reference to FIG. 6, in an embodiment of the invention, a method for prioritizing an image from an imaging modality is provided. In a first step 605, the PAPVR system retrieves images for review. Next, in step 610, the PAPVR system determines whether a reviewing or treating physician, such as a radiologist, would consider each image important. In an embodiment, step 610 can entail comparing each image to images from patients with known conditions to determine whether there is a match. In an embodiment, the PAPVR system can access an image database for image comparison. If the image under review is found by the PAPVR system to be important, in step 615 that image can be flagged as a "high priority" image. If the image is not found to be important (or if it is found to be unimportant), in step 620 that image can be flagged as "low priority." Next, in step 625, the PAPVR system prepares the images for review by a reviewing or treating physician.

In an embodiment, the PAPVR system can assign a priority value to an image based on the degree that the image matches one or more images from one or more patients with a known condition. Such matching can be accomplished by comparing the image under review by the PAPVR system to images from an image database. A higher priority value can be assigned to images that match known conditions (or physiological abnormalities) while a low priority can be assigned to images that do not match any known condition. For example, if an image under review matches an image from a patient with tension pneumo-thorax, that image can be assigned a high priority value. In some cases, a reverse priority value can be assigned, in which case a priority value is assigned based on the degree to which a given image matches one or more images from patients with no known conditions.

Case Prioritization

In another aspect of the invention, the PAPVR system can automatically prioritize patient cases. In various embodiments, the PAPVR system can automatically identify various medical conditions and assign that case a certain priority. The priorities assigned to the cases can be relative priorities (i.e., the PAPVR system determines that one case is of higher priority relative to another case in the queue of cases for a reviewing physician). Alternatively, the PAPVR system can prioritize cases based on absolute priority, which can entail prioritizing cases with patients having life-threatening conditions as high priority cases and patients without life-threatening conditions as low priority cases. The rules used by the PAPVR system to determine case priorities are configurable by the reviewing physician and the medical institution.

In an embodiment, the PAPVR system can automatically review a patient's images to determine whether the patient requires immediate medical care. If the PAPVR system determines that the patient requires immediate medical care, the PAPVR system can flag the patient's case as high priority. Otherwise, the PAPVR system can flag the patient's case as a lower priority (e.g., medium priority, low priority) case.

Figure 7:
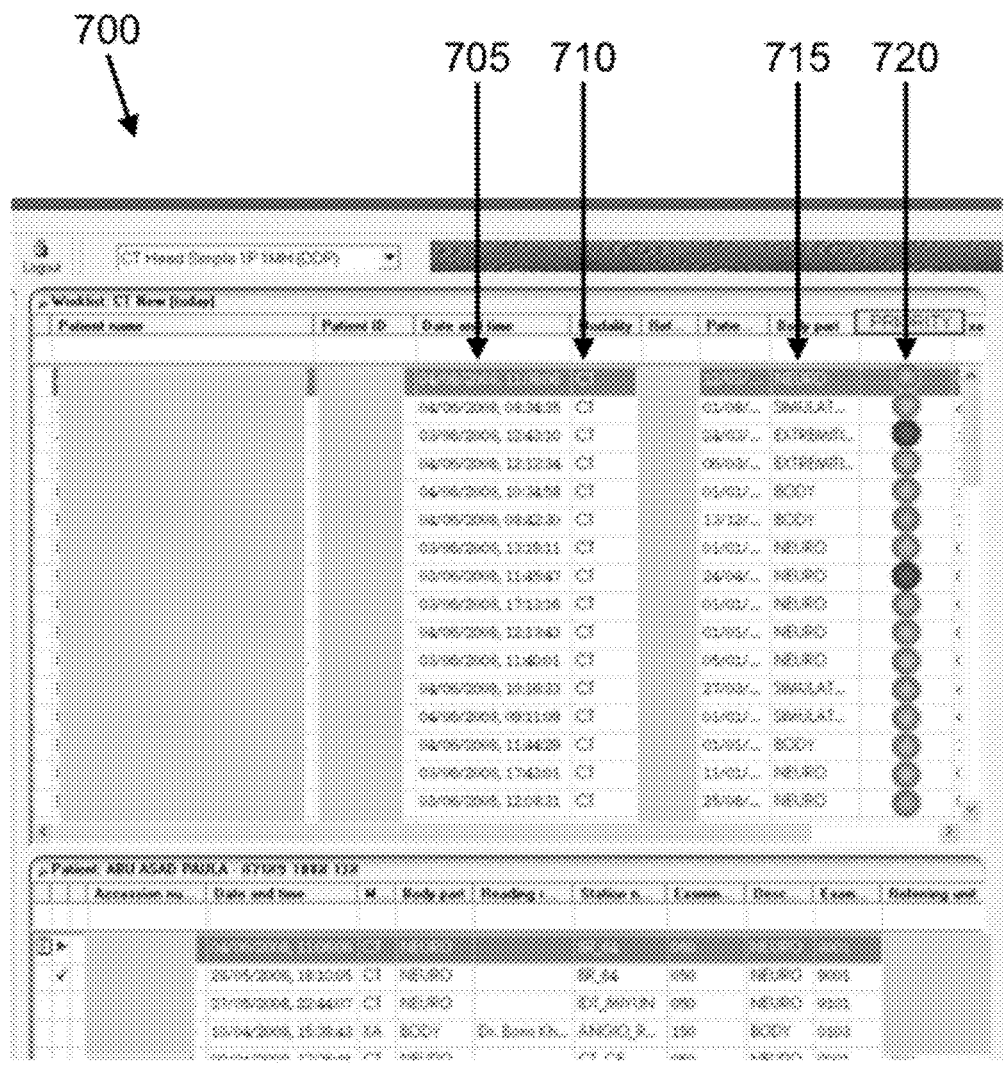
FIG. 7 is a screenshot of a patient case queue and the indication of priority of each case in the queue, in accordance with an embodiment of the invention.

With reference to FIG. 7, a screenshot of a patient case queue for a reviewing physician 700 is shown. The case queue includes a column 705 having a date and time stamp for each case, a column 710 with the modality (e.g., CAT/CT scan, MRI, PET/CT scan) used to acquire images, a column 715 showing the body part associated with each case, and a column 720 showing the priority associated with each case. The priority for each case can be indicated by a colored circle, with the color red indicating high priority, the color orange indicating medium priority, and the color green indicating low priority. Alternatively, the priority for each case can be indicated by a numerical value (e.g., 1-10, 1-100, 1-1000).

In an embodiment of the invention, the PAPVR system can automatically update case priorities. This can advantageously enable a reviewing physician, such as a radiologist, to be aware of the highest priority cases, such that these cases are reviewed first by the reviewing physician, and thus enable the referring or treating physician to get the reviewing physician's report sooner than if all cases were assigned the same priority. This capability of the PAPVR system can significantly shorten the time interval between when a patient is tested (e.g., with a CAT/CT scan, MRI, PET/CT scan) and when a patient is treated by the referring or treating physician after receiving the report from the reviewing physician. For example, if a case queue (such as queue 700 of FIG. 7) includes 10 cases with 1 case having high priority, 5 cases having medium priority and 4 cases having low priority, after the high priority case has been reviewed, the PAPVR system can reclassify the 9 remaining cases. This might entail reprioritizing the cases. In such fashion, the priorities assigned to the cases might be relative priorities (i.e., one case is of higher priority relative to another case). Alternatively, the PAPVR system can prioritize cases based on absolute priority, which might entail prioritizing cases with patients having life-threatening conditions as high priority cases.

In some embodiments, the PAPVR can optionally sort cases by priority. In an embodiment, the PAPVR system can sort cases in descending order based on priority. For example, the PAPVR system can display high-priority cases at the top of the queue and low priority cases at the bottom of the queue.

Case Review and Reporting

In an aspect of the invention, the PAPVR system can provide one or more images associated with a particular patient, in addition to data associated with each image, to a radiologist (or other reviewing physician) for review. In a preferable embodiment, the PAPVR system provides a radiologist an assessment of each image. In an embodiment, the PAPVR system can determine whether a particular ailment or abnormality is present in an image, and provide its assessment (e.g., "A pleural effusion has been detected") to a reviewing physician. The PAPVR system of preferable embodiments of the invention can enable improved patient outcomes and increased productivity.

Figure 8:
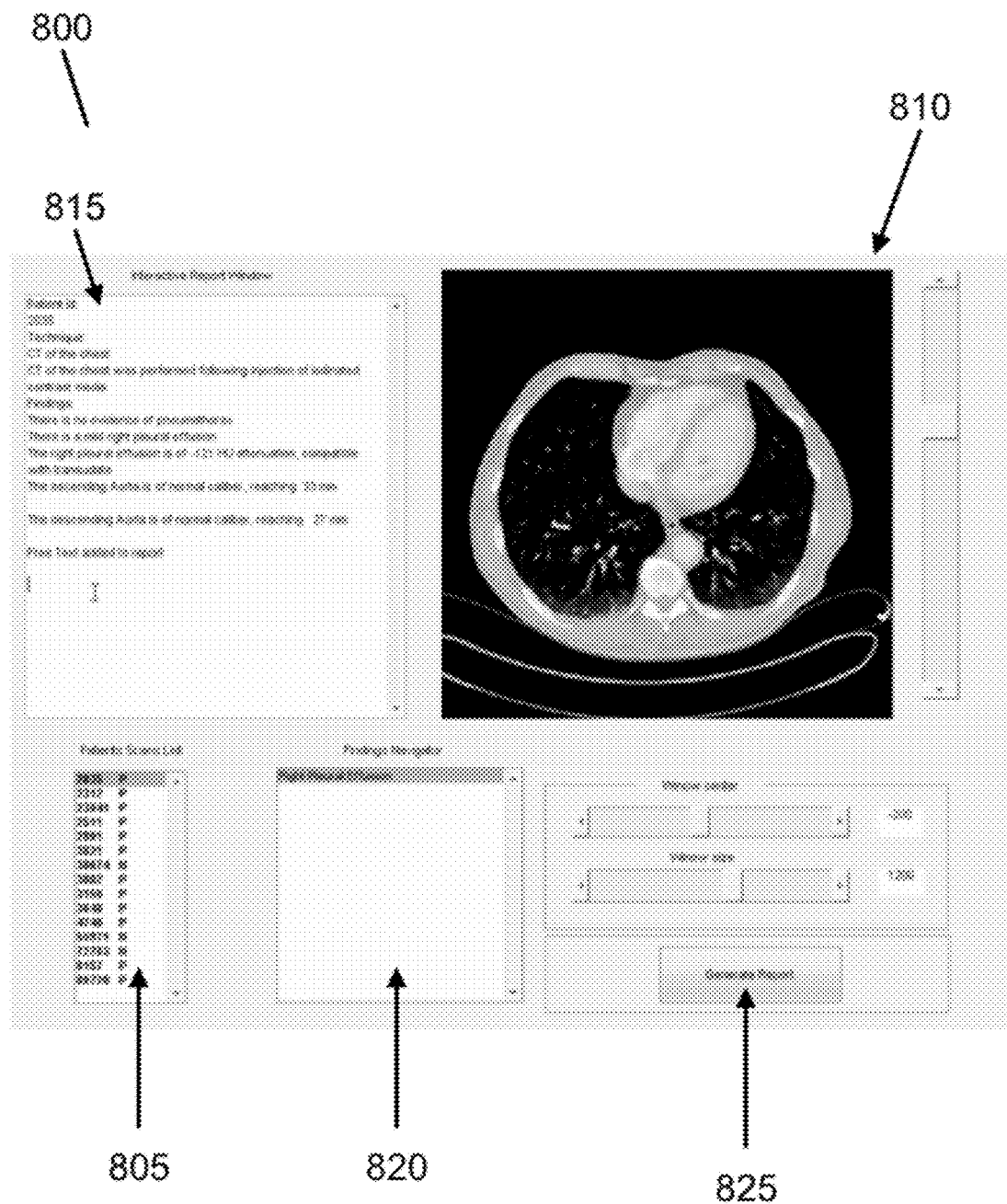
FIG. 8 is a screenshot of an interactive window, in accordance with an embodiment of the invention.

FIG. 8 an interactive window 800 that enables a radiologist to review images associated with each case, in addition to data provided by the PAPVR system. The interactive window 800 can also permit a radiologist to provide notes, including her/his assessment of the patient's condition. With continued reference to FIG. 8, the interactive window 800 includes a case or scan selection panel (or list) 805, a window 810 for displaying an image selected from the panel 805, an interactive report window 815 with information relevant to each image in the image window 810, a findings navigator window 820 that indicates the ailments or conditions (e.g., right pleural effusion) identified by the PAPVR system for the reviewed scan, and menu features 825 to permit a radiologist (or other reviewing physician) to generate a report and change the image visualization parameters (e.g., contrast or brightness), resize and center the window 810. The interactive report window 815 can include the patient's identification ("ID") number, the modality (CAT/CT scan, MRI, PET/CT scan) used to acquire the images, and the PAPVR system's assessment of the patient's condition. The interactive report window 815 can include other information, such as whether the priority associated with the patient's case, whether the image displayed in the window 810 is a Key Image, and whether the image displayed in the window 810 is a high priority image. The interactive report window 815 also permits a radiologist to provide additional information, such as additional findings with respect to the image shown in the window 810, and to edit the information provided by the PAPVR system.

In various embodiments, the findings navigator window 820 can be used by the reviewing physician to quickly navigate to and visualize in the image display window 810 Key Images the PAPVR system automatically associated with each of the findings that are listed in the findings navigator window 820. The PAPVR system can automatically adjust the visualization parameters of the image (e.g., contrast, brightness), or part of the image (e.g., highlighting the body organ in which an ailment was detected by the PAPVR system) displayed in the image display window 810 to help the reviewing physician better see or visualize the particular finding or findings.

In an embodiment, a PAPVR system prioritizes cases and provides the cases for review by a reviewing physician, such as a radiologist. The radiologist can use a computer terminal in communication with the PAPVR system to select the case of highest priority from the case queue (such as case queue 700 of FIG. 7). In an embodiment, the radiologist can use a reviewing system, such as the reviewing system 320 of FIG. 3, to retrieve a case. Next, the PAPVR system provides the radiologist an interactive window (such as interactive window 800 of FIG. 8) with images (e.g., two-dimensional cross-sections) from a particular region of a patient's body. In the interactive window the PAPVR system can provide its assessment of the patient's condition. The PAPVR system can permit the radiologist to provide additional information to the patient's case. The PAPVR system can also provide a radiologist additional information relevant to a particular image, such as distances, cross-sectional areas, and volumes.

Systems

The disclosure provides computer systems for implementing the methods provided herein. A computer system can be a computer server ("server") that can be configured (e.g., programmed) to retrieve, process and analyze medical images. The server, in some examples, can include a data communication interface for packet data communication. The server can also include a central processing unit (CPU), in the form of one or more computer processors (also "processors" herein), for executing program instructions. The server platform can include an internal communication bus, program storage and data storage for various data files to be processed and/or communicated by the server, although the server can receive programming and data via network communications. The hardware elements, operating systems and programming languages of such servers are conventional in nature, and it is presumed that those skilled in the art are adequately familiar therewith. Of course, the server functions can be implemented in a distributed fashion on a number of similar platforms, to distribute the processing load.

Aspects of the methods outlined herein can be embodied in programming. Program aspects of the technology can be thought of as "products" or "articles of manufacture" typically in the form of executable code and/or associated data that is carried on or embodied in a type of machine-readable medium. "Storage" type media can include any or all of the tangible memory of the computers, processors or the like, or associated modules thereof, such as various semiconductor memories, tape drives, disk drives and the like, which can provide non-transitory storage at any time for the software programming. All or portions of the software can at times be communicated through the Internet or various other telecommunication networks. Such communications, for example, can enable loading of the software from one computer or computer processor (also "processor" herein) into another, for example, from a management server or host computer into the computer platform of an application server. Thus, another type of media that can bear the software elements includes optical, electrical and electromagnetic waves, such as used across physical interfaces between local devices, through wired and optical landline networks and over various air-links. The physical elements that carry such waves, such as wired or wireless links, optical links or the like, also can be considered as media bearing the software. As used herein, unless restricted to non-transitory, tangible "storage" media, terms such as computer or machine "readable medium" refer to any medium that participates in providing instructions to a processor for execution.

Hence, a machine-readable medium can take many forms, including but not limited to, a tangible storage medium, a carrier wave medium or physical transmission medium. Nonvolatile storage media include, for example, optical or magnetic disks, such as any of the storage devices in any computer(s) or the like, such as can be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media can be involved in carrying one or more sequences of one or more instructions to a processor for execution.

Various features of systems and methods of the disclosure may be implemented with the aid of applications (or "apps") operated on electronic devices, such as portable electronic devices. Portable electronic devices can include portable computers (e.g., Apple® MacBook Pro), tablet personal computers (e.g., Apple® iPad, Samsung® Galaxy Tab), and Smart phones (e.g., Apple® iPhone, Android-enabled phones).

Figure 9:
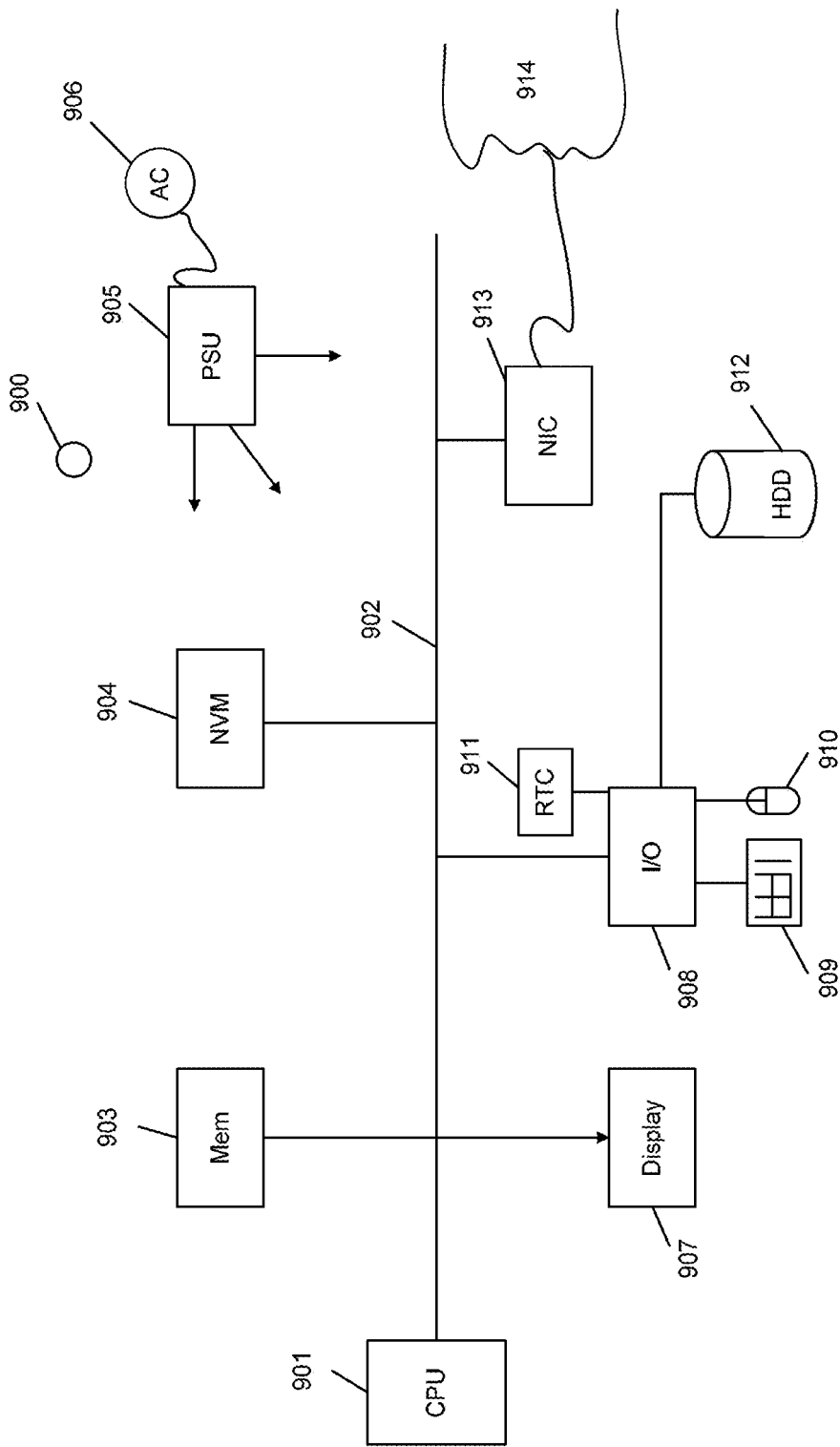
FIG. 9 is an exemplary overview of a computer system as may be used in any of the various locations throughout the system and method disclosed herein.

FIG. 9 schematically illustrates computer system 900 that can be used with systems and methods of the disclosure. The computer system 900 can be used to execute code to process data. Various modifications and changes may be made to computer system 900 without departing from the broader spirit and scope of the system and method disclosed herein. A central processing unit (CPU) 901 is connected to a bus 902, which bus is connected to a memory 903, nonvolatile memory 904, display 907, I/O unit 908, and network interface card (NIC) 913. I/O unit 908 may, typically, be connected to keyboard 909, pointing device 910, hard disk (or in some cases other suitable storage, including, but not limited to solid state disk, RAID, network attached storage, storage area network, etc. 912, and real-time clock 911. NIC 913 connects to network 914, which may be the Internet or a local network, which local network may or may not have connections to the Internet. Also shown as part of system 900 is power supply unit 905 connected, in this example, to ac supply 906. Not shown are batteries that could be present, and many other devices, including but not limited to special enhanced pointing or navigational devices, such as mice, jog wheels, etc, microphone(s) and speaker(s) and/or headset(s) for recording and or playing back audio, and other modifications that are well known but are not applicable to the specific novel functions of the current system and method disclosed herein.

Figure 10:
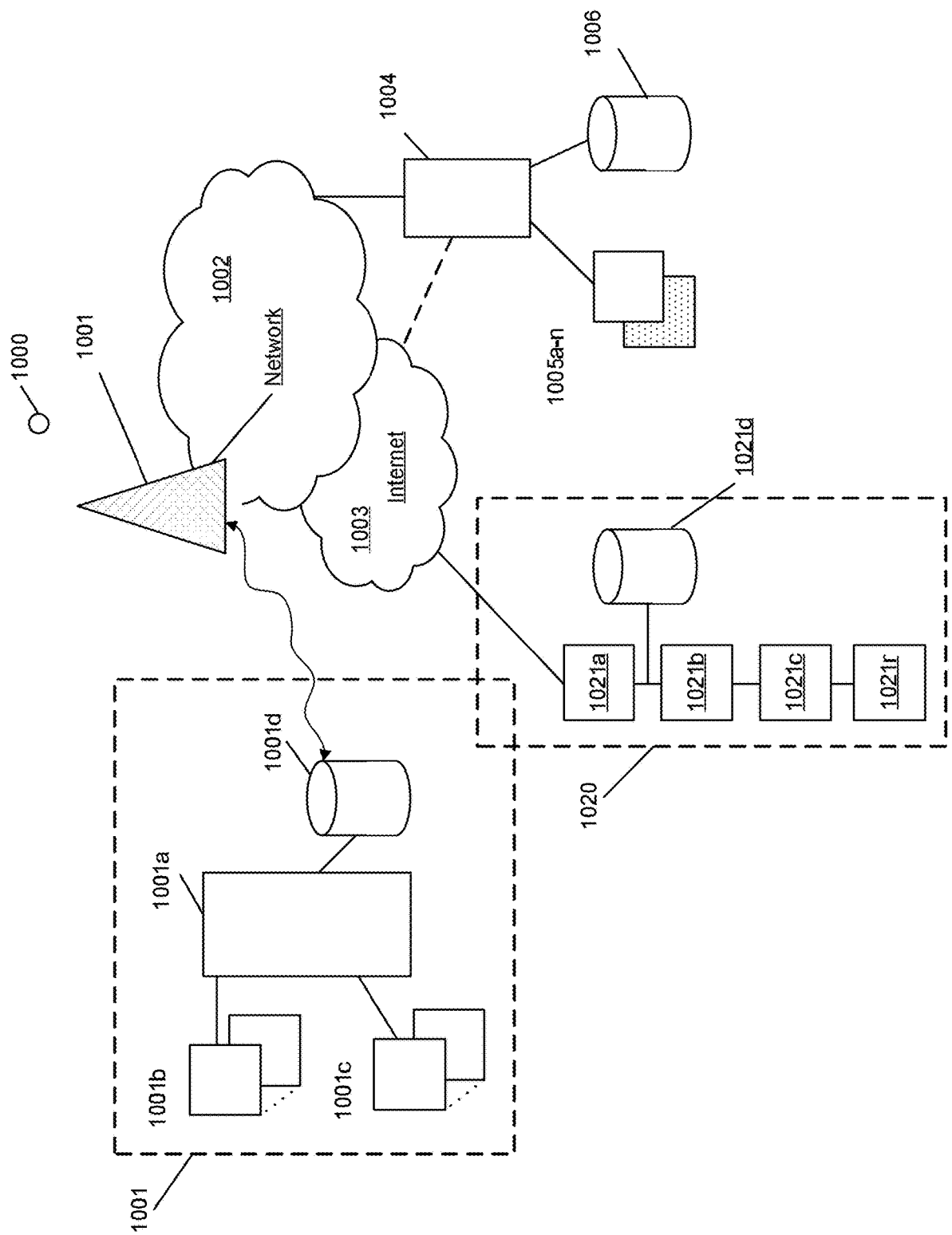
FIG. 10 is an exemplary overview of a network-based system, in accordance with an embodiment of the invention.

FIG. 10 shows a simplified overview of an exemplary PAPVR system 1000 in an Internet- or other network-based implementation, according to one aspect of the system and method disclosed herein. In an embodiment of the invention, the PAPVR system can be seen as a software 1005x running on server 1004 connected to a network 1002 (the Internet or a private network, or combination), having a local repository 1006, as well as additional software instances 1005a-n including such as operating system, networking software, image processing software and any other suitable or needed software. The system presents all images acquired from an imaging modality (e.g., CAT/CT scan 1021a, MRI 1021b, PET/CT scan 1021c, etc.) in one exemplary location in a hospital 1020 to a reviewing physician at a terminal or computing device 1021r in said hospital. In this example, the PAPVR is off site, and the physician views images in the hospital, but processing may happen off site. Additionally, patient data may be encrypted, so patient confidentiality is protected, etc. In an embodiment, the PAPVR system can first present the reviewing physician with the one or more Key Images (and data associated with the one or more representative images) and provide the reviewing physician the option to review the other (i.e., non-representative) images. In an embodiment, the non-representative images (and data associated with the non-representative images) can be viewed after the reviewing physician has viewed the one or more Key Images. By prioritizing transmission of key images, valuable minutes in an emergency room can be saved, for example. Also shown is a local storage 1021*d*.

Exemplary hospital 1001 may be in a remote location and use wireless communication to provide the same services to its physicians and patients, etc., having the same or similar equipment 1001 *a-n*, analogous to 1021*a-n*.

Figure 11:
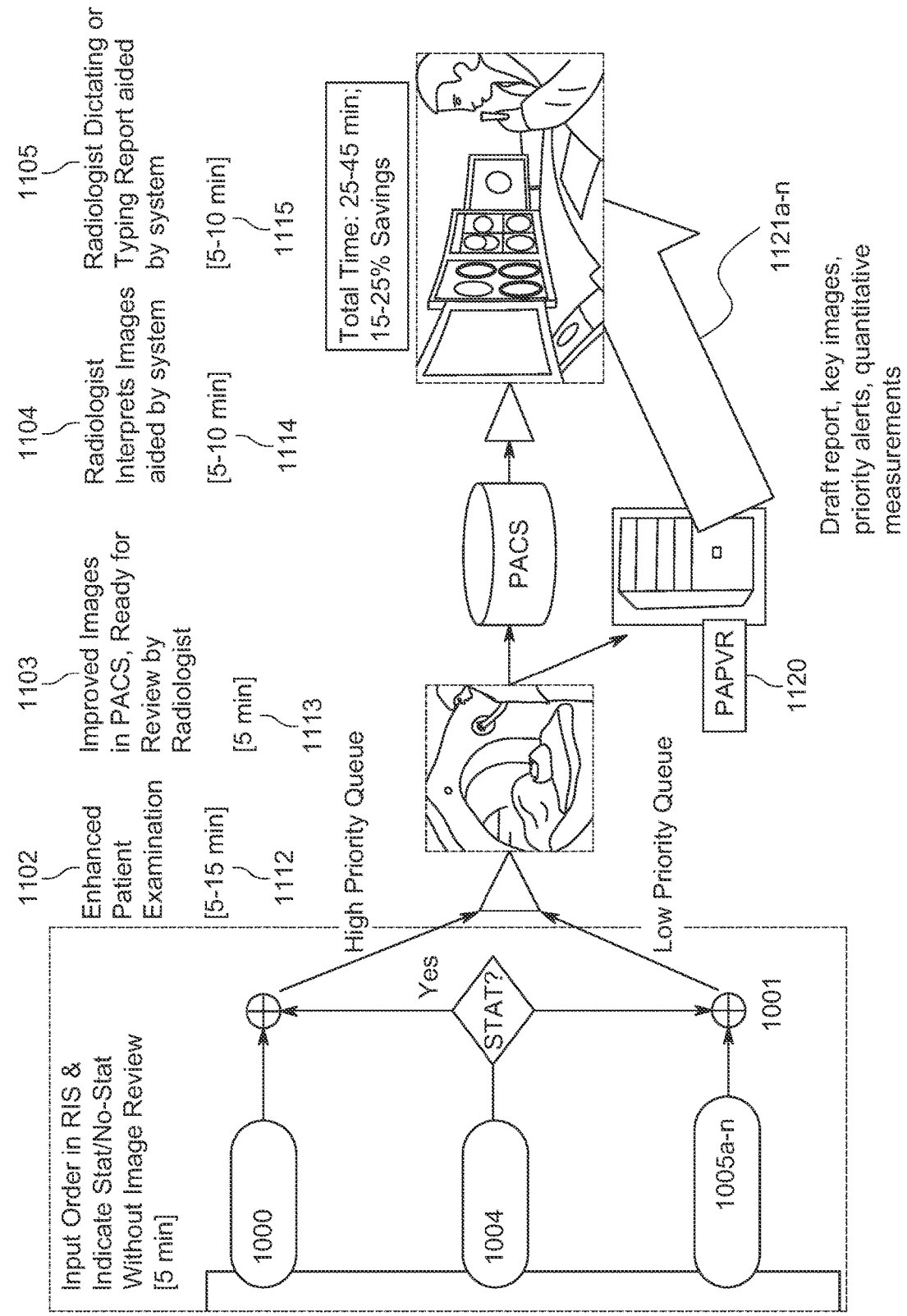
FIG. 11 is an exemplary revised timeline for the medical imaging workflow shown in FIG. 1, in accordance with an embodiment of the invention.

FIG. 11 shows an enhanced work flow with work times amended from those in FIG. 1, showing the time savings for steps for enhanced steps 1102, 1103, 1104 and 1105, which are analogous to, but improved as described herein, steps 102, 103, 104 and 105 of FIG. 1, with respectively revised times 1112, 1113, 114, and 1115. The PAPVR system 1120 generates items 1121*a-n* for the physician and other medical personnel.

In some other embodiments, the PAPVR system may present the reviewing physician the images in order of priority. In some embodiments, only the higher priority images may be displayed to the reviewing physician. Alternatively, all of the images, starting with the higher priority images may be displayed to the physician.

In some embodiments, the system may use a Key Image, or a high priority image, to assist a physician with generating a report. In some embodiments, the default images for a report may be Key Images. A physician may be presented with the option of changing the image for the report. Alternatively, the physician may make an initial selection of the image(s) to be included within the report. This may help streamline the medical review process, and the report generation process.

While various embodiments of the invention have made reference to a "scan" or "scans," it will be appreciated that any use or reference to a "scan" or "scans" can refer to any type of image. In an example, a "scan" refers to a medical image or a diagnostic image. In another example, "scans" refer to multiple medical images.

It will be appreciated that PAPVR systems and methods described in various embodiments of the invention can be integrated in (or used with) other systems and/or methods, such as, for example, medical or diagnostic systems and/or methods, both in part or in whole.

Enhanced Patient Outcome Tracking

In another aspect of the invention, systems and methods for patient outcome tracking are provided. In some embodiments, processes for tracking outcomes of final reports are described.

In some embodiments, methods for providing medical diagnostic images comprise retrieving, using a processor, one or more images from an image database or an imaging device, the one or more images defining a set of images. Next, one or more images from the set of images are selected based on diagnostic data stored within a memory. Next, a report is generated including the one or more selected images, and the report is provided to a reviewing physician. One or more modifications to the report are received from the reviewing physician. The diagnostic data is then updated based on the one or more modifications. The memory may be formed of one or more databases. In some situations, one or more additional images defining an additional set of images are retrieved using a processor, and one or more images are selected from the additional set of images based on the updated diagnostic data.

In some cases, the diagnostic data is stored in a diagnostic table, and updating diagnostic data includes updating the diagnostic table. The diagnostic table is stored in a memory location.

In some embodiments, methods for providing medical diagnostic images comprise retrieving, using a processor, one or more images from an image database or an imaging device, the one or more images defining a set of images. Next, one or more images from the set of images are selected based on diagnostic data stored within a memory. Next, a report is generated including the one or more selected images, and the report is provided to a reviewing physician. Patient outcome information relating to patient responsiveness to treatment is received, and the diagnostic data based on the patient outcome information is updated. In some cases, the methods comprise receiving a clinical diagnosis for a patient associated with the set of images, receiving initial radiological findings for the patient, retrieving one or more images multiple times during treatment of the patient, and determining whether the initial radiological findings were supported.

In some situations, the diagnostic data is updated with information related to the discrepancy (also "discrepancy-related information" herein) if the initial radiological findings were not supported. One or more modifications to the report may be received from the reviewing physician, and the diagnostic data may be subsequently updated based on the modification.

Figure 12:
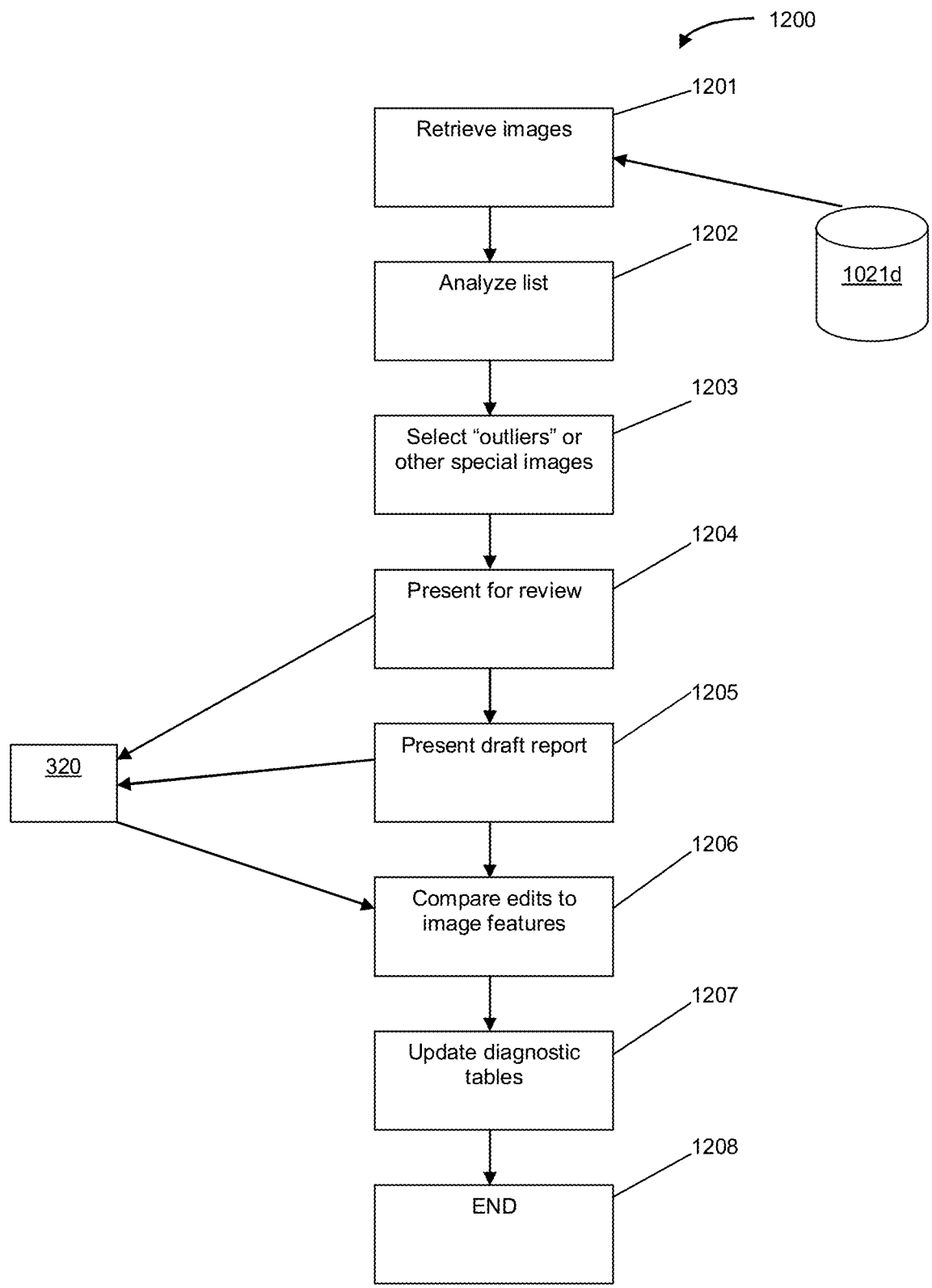
FIG. 12 shows an exemplary process for tracking outcomes of final reports and matching to differences in images.
Figure 13:
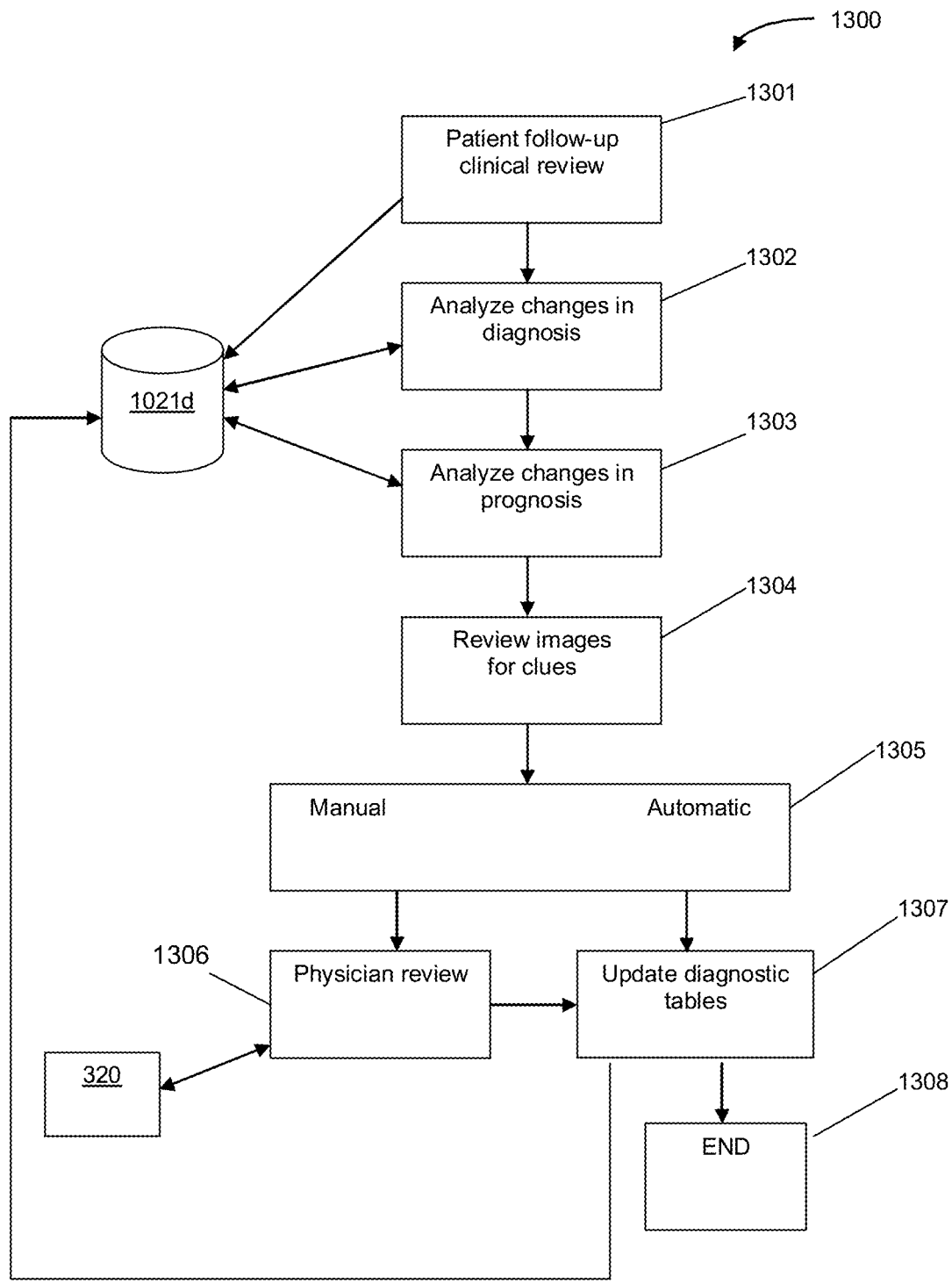
FIG. 13 shows an exemplary process 1300 for follow-up of post-visit patient history.

FIG. 12 shows an exemplary process 1200 for tracking outcomes of final reports and matching to differences in images, in accordance with an embodiment of the invention. In step 1201, a list of images, with the images accessible or attached thereto, is received from a repository 1021*d*. Any networked or otherwise connected (or operatively coupled) repository may be used in addition to, or in lieu of, repository 1021*d*. In step 1202, this list is analyzed with the images available for this case. Next, in step 1203, the system selects "outlier" images that have strong characteristics that deviate from a normal image and therefore are most likely to be representative of the specific condition. The selection in step 1203 can be made with the aid of a processor. In step 1204 those images are presented for review by a user, and in step 1205 the system generates and presents a draft report to a physician or other qualified medical personnel for review. The images may be reviewed by a user with the aid of a screen 320. Next, in step 1206, after a reviewer edits or modifies the report, the system compares the edits and reviews the images again to determine whether the changes in the report are supported by recognizable differences in the images or other deviations from the standard images that represent the patient's original diagnosis. The comparison in step 1206 can be made with the aid of a processor. Then, in step 1207, diagnostic tables are updated for future use, according to changes and differences found, and then in step 1208 the procedure ends. The update in step 1207 can be made using a processor.

FIG. 1300 shows an exemplary process 1300 for follow-up of post-visit patient history, in accordance with another embodiment of the invention. From time to time the system updates and collects information from other databases, such as referring doctors, hospitals, clinics, research data, etc. In step 1301, the follow-up data is accessed or downloaded, typically over a network, and analyzed. It is typically added to the repository, again, in this example, repository 1021*d*, which may be any networked or otherwise connected repository as described herein. In some situations, the repository 1021*d* includes one or more physical storage mediums, such as flash memory, random access memory and/or hard drives. The repository 1021*d* may be a database operatively coupled to the system, such as over an intranet or over the Internet (e.g., World Wide Web).

Next, in step 1302, the newly obtained data or data sets are analyzed for changes in diagnosis indicating a potential problem in the previous diagnosis, or just a progression of the patient's condition, for better or worse. In step 1303, the changes are analyzed for resulting changes in prognosis. In step 1304, the images are analyzed for additional clues differentiating at least one of the previous images from the standard image(s) for the initial diagnosis, allowing the system to refine its diagnosis capabilities. In step 1305, the process splits into a "Manual" work flow and an "Automatic" workflow. Moving to step 1307, the original patient images, and in some cases reference images and analysis tables, are updated automatically. Alternatively, moving to step 1306, with help of a physician or otherwise qualified personnel performing an additional manual review on screen 320, the findings proposed by the system are confirmed or corrected. When the physician has reviewed the images, the information is updated in step 1307 (as it was in case of only an automatic review) and the procedure ends in step 1308. The purpose of this optional review is to refine the analysis tables with follow up data of the actual patients. The information is typically stored in a database that has one or more tables (e.g., multiple tables), including a standard object and deviation from the norm, and thus refine continuously the system's decisions. There are many different approaches according to which such additional data may influence future diagnostic models, and different outcomes may translate to better images analysis.

For example, the system may report "moderate" findings for a case such as pleural effusion. In system analyses over time, the same finding is reported over time for many patients as "severe." The system then learns and adapts automatically the severity range table. This effect is achieved by the system automatically updating its lookup tables for the severity of findings based on its quantitative measurements of each finding.

In another example, in a report a radiologist may use different and/or additional key images to the key images automatically reported by the system. The system then automatically lears from these examples and corrects and adjusts its algorithms accordingly for improved key image selection and/or gray scale windowing.

Alerts to Various Participants

In another aspect of the invention, systems and methods are provided for raising alerts for urgent medical conditions, whether they were anticipated or not, and, based on those alerts, immediate emergency response may be requested, or additional review by another radiologist or other qualified personnel. The system may also have a decision support system where additional clinical findings can be checked to determine whether the alert should have been raised or not, and added visualization that highlights the items that led to the raising of the alert. Alerts provided to a radiologist on duty and/or referring physician could be in the form of an automatic phone call, short message service (SMS) text message, multimedia messaging service (MMS) text message, or email to which a summary of key critical findings may be attached to show salient information, such as, for example, key images or measurements. Additionally, the enhanced system and method disclosed herein may prioritize a radiologist's work list by leveraging CAD findings to analyze a patient's condition and designate case priorities within the work list. Information from enhanced analytics may be used create flags within the radiologist work list, such as, for example, designating a case as high, medium, or low priority. This information may also be used to control the order of the cases in the work list such that a higher-priority case is placed above a lower-priority case.

In some embodiments, a method for providing medical diagnostic images comprises retrieving, using a processor, one or more images from an image database or an imaging device, the one or more images defining a set of images. One or more boundary parameters are then obtained from a memory. Next, using a processor, the system determines whether each of the images falls within the boundary parameters. Next, one or more alerts for an urgent medical condition are provided if one or more of the images falls within the boundary parameters. The one or more alerts may be raised to request an immediate emergency response.

In some embodiments, a system for providing medical diagnostic images comprises an imaging modality for retrieving medical diagnostic images from a patient; a database comprising one or more boundary parameters; a processor configured to compare the retrieved images with the one or more boundary parameters; and an alert system in communication with the imaging modality and database configured to provide one or more alert for an urgent medical condition if one or more of the images falls within the boundary parameters. In an embodiment, the boundary parameter is the volume of air within a thorax or outside one or both lungs. In another embodiment, the alert system is configured to provide the one or more alert without intervention or review by a physician. In another embodiment, the system further comprises a prioritizing, visualization and reporting system (or sub-system) in communication with the imaging modality and reviewing system, wherein the prioritization, visualization and reporting system is configured to: retrieve one or more images from the imaging modality, the one or more images defining a set of images; and determine whether one or more of the images is representative of the set of images and provide the one or more images to the reviewing system, wherein the one or more images are provided with an image that is representative of the set of images.

Figure 14A:
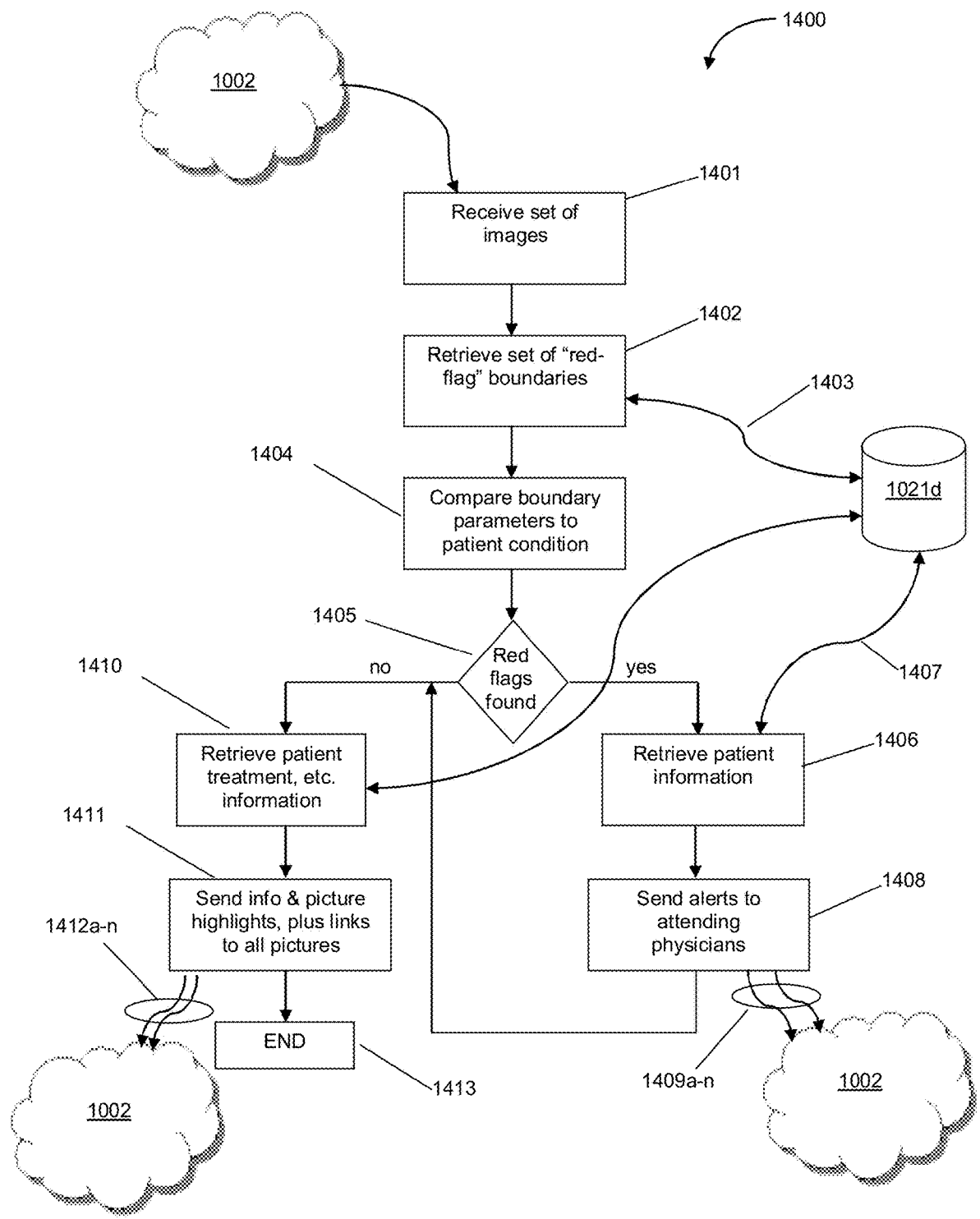
FIG. 14a shows an exemplary process for implementing an enhanced alert system.

FIG. 14*a* shows an exemplary process 1400 for the implementation of an enhanced alert system, in accordance with an embodiment of the invention. In step 1401*a* set of images is received by the system from cloud 1002 from one of the other processing elements as discussed herein. In some embodiments, the set of images, which include one or more images, are retrieved with the aid of a processor. The cloud 1002 may include one or more computer systems operatively coupled to the system through the Internet, an intranet, or both. In some cases, the process may begin after only part of the set of images is received; in other cases, the system may wait until all images are received, or it may begin after receiving only part of the set, and then go through the process again after receiving all the images in a set. In step 1402 a set of red-flag boundaries are retrieved from a database (also "data base" herein), such as, for example, database (or data repository) 1021*d*, the retrieval occurring at the end of a request-and-response process 1403. In step 1404 the system compares data from the processed images to the flag list parameters to determine whether certain boundaries are exceeded, either minimally or maximally. For example, if the volume of air in the thorax outside one or both lungs, a condition known as pneumothorax, exceeds a level determined by one of the parameters in the flag list, there is an acute danger of the lung collapsing. Thus when the ratio of the volume of air outside the lung to the overall thorax, for example, goes below a certain boundary, the system sets a red flag. In step 1405, the system checks for a red flag. If the system finds a red flag ("yes"), the process moves to step 1406, where the system retrieves patient information, including all referring and specialist physicians involved in treatment. In step 1408 the system sends an alert 1409*a-n* to all discovered physicians. These alerts may be automated telephone messages, pager alerts, emails, text messages (e.g., SMS text messages, MMS text messages), or any combination thereof, such as, for example, a pager alert notifying the physician of an urgent email. If, in step 1405, the system does not find a red flag ("no"), and also after step 1408, the process moves to step 1410, where additional information about the patient's treatment history and any other pertinent facts about the case may be retrieved from a database, such as database 1021*d* or any other database or data repository. In step 1411, the system sends the retrieved information, pictures highlights, and links to more detailed information and pictures via communication methods 1412*a-n* to all medical personnel involved in the patient's treatment, which communication methods 1412*a-n* may be similar to communication methods 1409*a-n*. In step 1413 the process ends.

Figure 14B:
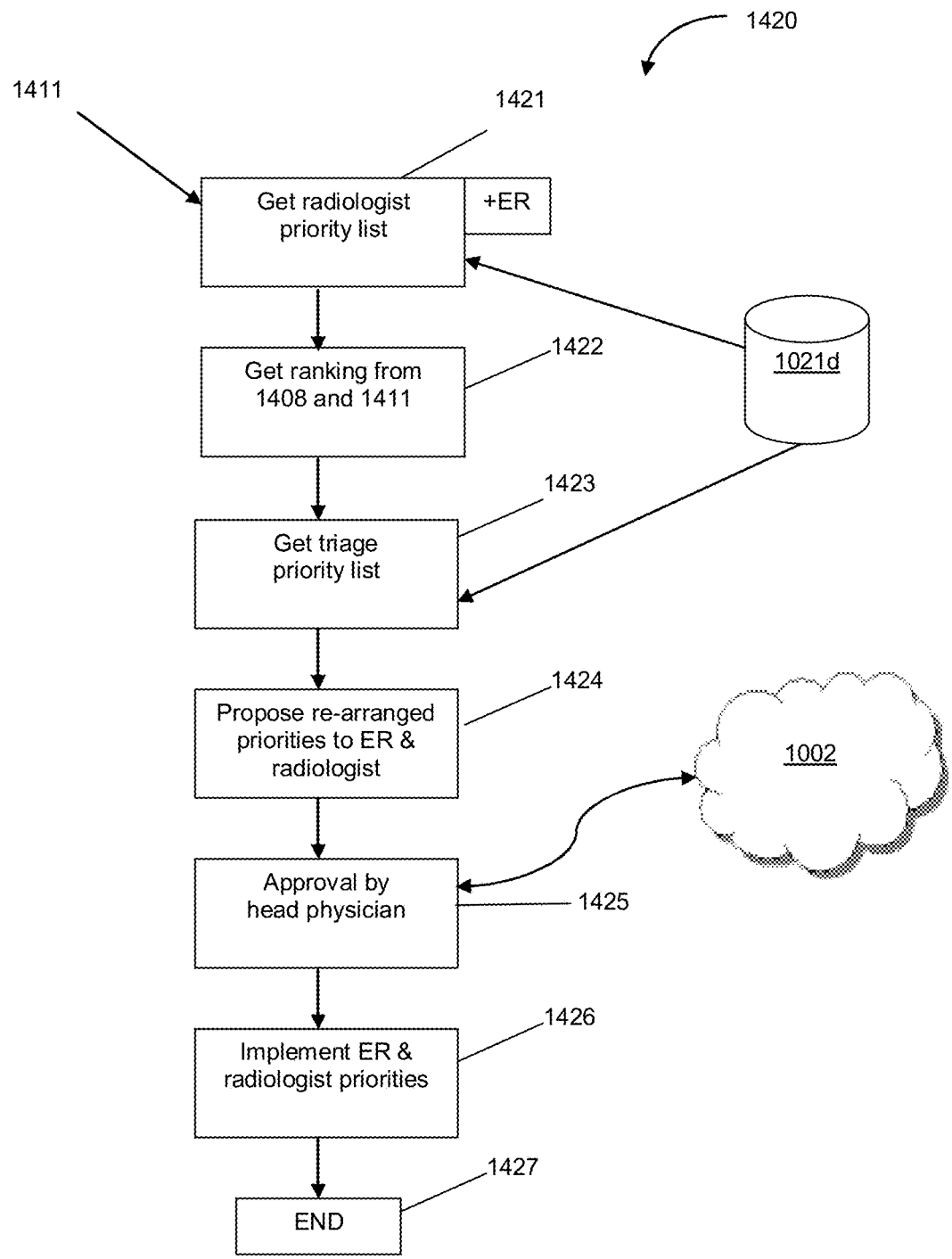

FIG. 14*b* shows an exemplary process 1420 for an optional continuation from step 1411 of process 1400, in accordance with an embodiment of the invention. In step 1421, the system retrieves the priority list of the radiologist and the ER from database 1021*d* or other database. This list may pertain to the treatment of the particular patient who is the subject of the alert in process 1400 above, or be a general occasional rearrangement, or a combination of both instances. In step 1422, the system gets priority rankings from steps 1408 and 1411, described above. In step 1423, the system likewise gets a triage priority list, again from database 1021*d* or other data base. In step 1424 the system proposes a re-arranged priority list to the ER and the radiologist. In step 1425 the system receives approval from the physician or physicians in charge, including but not limited to physicians in charge of the ER, the radiologist, and, if applicable, a specific patient's treatment. In step 1426 the system implements the rearranged priorities list, and in step 1427 the process ends.

In some embodiments, systems and methods disclosed herein, such as PACS systems or PAPVR systems, provide enhanced analytics of medical diagnostic images based on the history of the patient and comparable data, using preimposed historical data from the patient, to further enhance analytics and then compare the patient's current images to the patient's historic images, while also comparing the images against peer group images and to the outcome histories recorded in the analytical database ("DB") to further improve analytics. This approach is based on smart filtering that uses various methods as described throughout herein to detect various medical conditions and to track a patient's progress.

In some embodiments, methods for providing patient medical diagnostic images comprise retrieving, using a processor, one or more images associated with a patient from an image database or an imaging device, the one or more images defining a set of images. Next, historical data of the patient is retrieved from a memory. Using a processor, the one or more images are compared with the historical data. The one or more images and the historical data are then provided to a reviewing physician.

In some embodiments, a system for providing medical diagnostic images comprises an imaging modality for retrieving medical diagnostic images from a patient; a database comprising historical data of said patient; a processor configured to compare the retrieved images with the historical data of said patient; and a prioritizing, visualization and reporting system in communication with the imaging modality and the database configured to provide the images and the historical data to a reviewing physician.

In some situations, the system uses prior cases of same patient and also brings similar cases from a knowledge base, rather than from the same patient. A medical technician or other qualified individual then identifies specific attributes in the current case and uses those attributes to search a comprehensive medical data base so that similar cases can be obtained to help a radiologist diagnose the current case. More specifically, the system retrieves relevant medical article on a subject disease and finds patient comparables for statistical information on this subject disease and/or patients. It then extracts time-dependent attributes (comparisons of two or more time points, e.g., clinical measurements, such as volume of pneumothorax); and it includes attributes, measurements, statistics, examples from similar cases, as well as relevant publications, in a preliminary report for a radiologist to use in creating a final report to the referring physician. The time dependent attributes may be extracted periodically, such as at set intervals.

Figure 15:
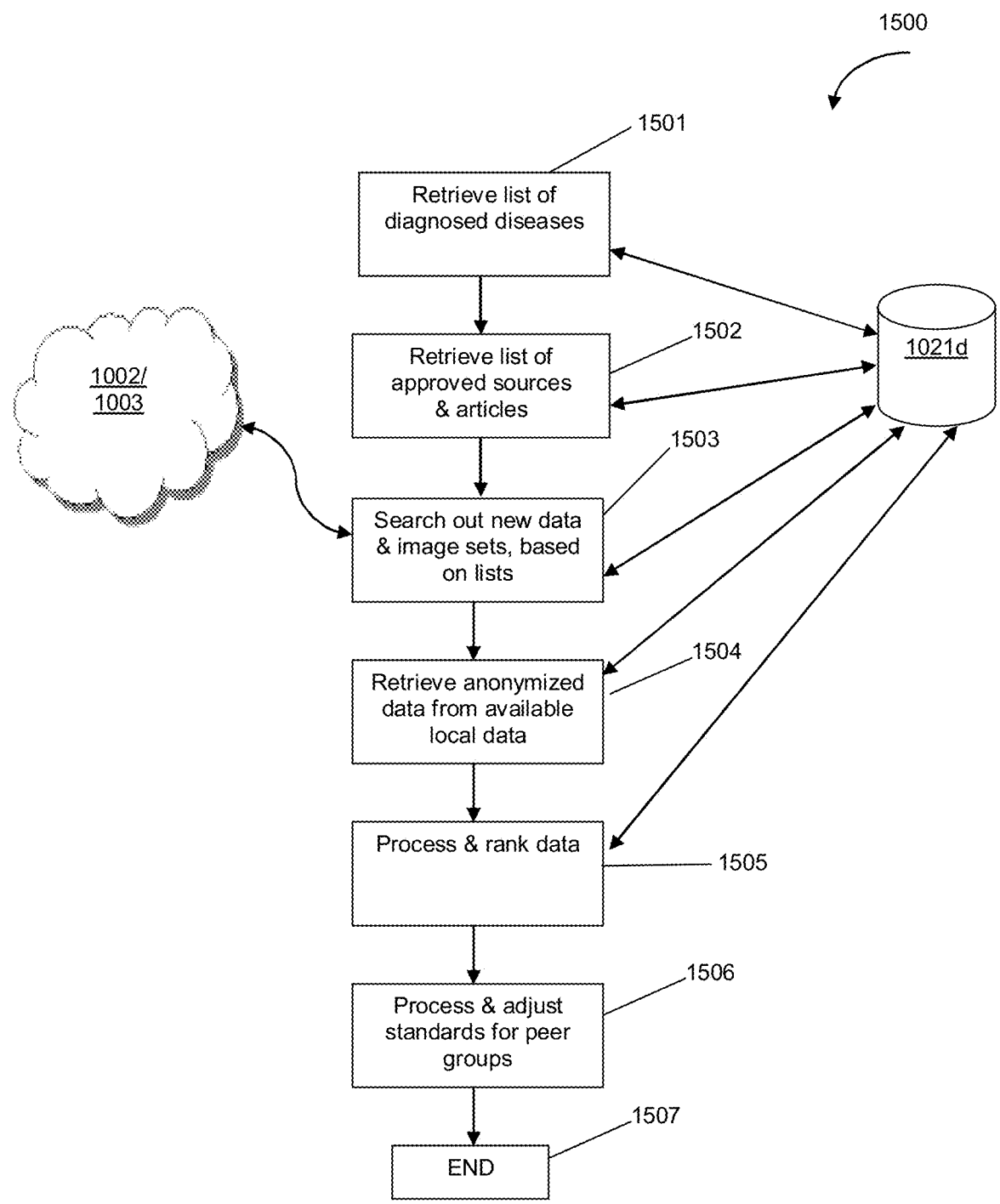
FIG. 15 shows an exemplary process for the implementation of an enhanced analytics system.

FIG. 15 shows an exemplary process 1500 for the implementation of an enhanced analytics system, in accordance with an embodiment of the invention. In step 1501 the system (e.g., PACS system, PAPVR system) retrieves from a database, such as, for example, database 1021*d* or any other database, a list of diseases that it has previously diagnosed. In step 1502, the system retrieves from the same database a list of approved sources and previously retrieved articles. In step 1503, the system makes searches, based on the lists generated in steps 1501 and 1502, of its local database and of other sources throughout network 1002 and Internet 1003, and retrieves new articles, diagnoses, image sets, and other relevant data. In step 1504, the system retrieves anonymous subject (e.g., patient) data available from local databases, including diagnoses, history, etc. In step 1505 the system processes and then, based on the diagnosed diseases or conditions, as well as the physician's diagnosis of the patient and/or the patient history, etc. ranks all the retrieved articles. In step 1506 the system processes and adjusts the standards according to peer groups; that is, the system sorts data in multi-dimensional groups, according to such factors as patient age, gender, life style and habits (e.g., whether the patient smokes, whether the patient drinks excessively, whether the patient is single or married), disease, progression and stage of disease, etc. The system then uses this data to adjust standards for such condition descriptors as "normal," "at risk," "critical," etc. for patients in each group. The system may run process 1500 at a predetermined time period, such as daily, weekly, monthly, or more, which may be adequate to keep information up to date. The time period balances the effort of processing all the data and the latency in retrieving new data. In some cases, the time period is a fixed time period (e.g., every week), while in other cases the time period changes, such as, for example, from weekly to monthly or vice versa.

Figure 16:
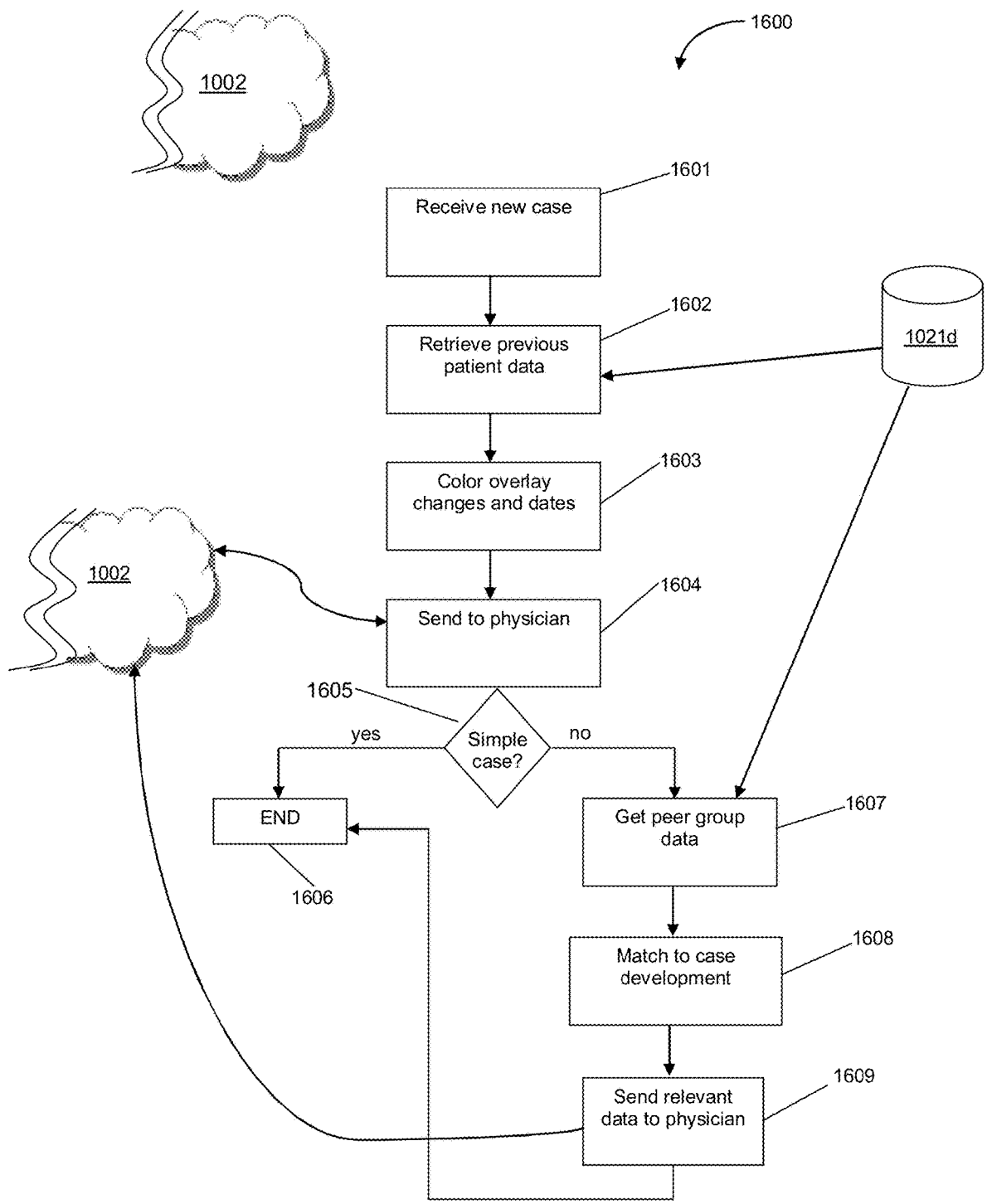
FIG. 16 shows an exemplary process for the analysis of patient medical data.

FIG. 16 shows an exemplary process 1600 for the analysis of patient medical data, in accordance with an embodiment of the invention. In step 1601 the system receives a new set of patient images for processing from network 1002. In step 1602 the system retrieves previous data about this patient from database 1021*d*. In step 1603 the system color codes (or uses other visual indicators) the changes, dates, etc. if more than one historic snapshot is available. In step 1604 the system sends the data to the patient's physician for review, via, for example, the network 1002. In step 1605 the system determines whether the case is simple or complex, based on analysis of retrieved articles and other data, plus peer group data. Cases may be characterized as simple or complex, for example, upon input from a reviewing physician, or via a machine learning algorithm that learns the types of cases one or more physicians consider simple and the types of cases one or more physicians consider complex. If the case is deemed simple ("yes"), the process ends at step 1606. If the case is not deemed simple ("no"), in step 1607 the system gets peer group data, as described above in the discussion of step 1506 of FIG. 15, from database 1021*d*. In step 1608 the system matches the retrieved peer group data against any new development in the case currently under analysis. In step 1609 the system sends any additional relevant information to the patient's physician, and then the process ends at step 1606. In some cases, if, at step 1605, the system has determined that the case is simple, the physician may request the system to treat the case as complex and retrieve and match peer group data. In other cases, the system is configured to treat all cases as complex and always execute steps 1607-1609.

Figure 17:
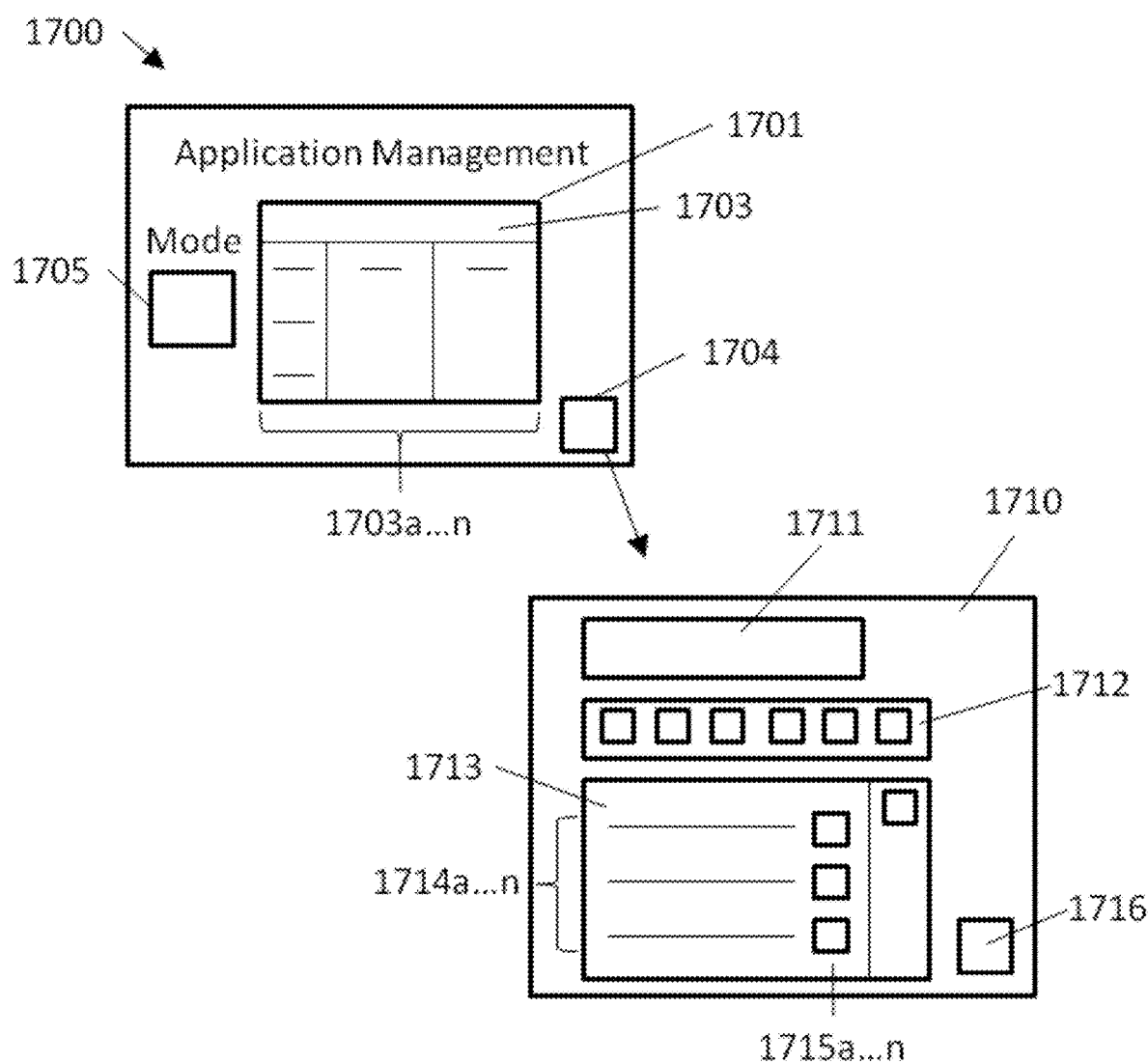
FIG. 17 shows two exemplary screens of systems and methods disclosed herein.

FIG. 17 shows two exemplary screens of various systems and methods disclosed herein. Screen 1700 is an application management screen, and screen 1710 is an application store screen. The screens may be part of a graphical user interface (GUI) of a system (e.g., PACS system, PAPVR system). The GUI may be stored in a machine readable medium (e.g., flash memory, cache, hard disk) and implemented by a processor of the system. The GUI may be part of an operating system or a software component of the system. A mode control area 1705 in screen 1700 shows the current mode of the system, and whether it is an approved or non-approved mode. A user may click on a button in area 1705 to toggle a mode on or off, or select a different mode from a list. One mode is typically specified as a default mode. In an example, in the United States, typically, the default mode may be an FDA-approved mode. In this mode, only FDA-approved modules and plug-ins are used. Any activation of other, non-approved modules automatically takes the system out of the default FDA-approved mode. The system in such a case provides a user a visual non-default mode indicator, such as, for example, a red blinking frame around the system screen display (see above), resulting in an overlay imprint on any images, films, etc., which renders certain modules and plug-ins non-approved for patient use. Screen 1700 also includes an application overview section 1701, with a header section 1702. Columns 1703*a-n* show the various modes and applications in the system and information about each app, such as their state (i.e., whether active or inactive), revision level, date downloaded, price, etc.

Display of some features of the application management screen may be blocked or modified by a system management console (not shown) that only a system administrator can control. In an example, only the administrator (or other user with the requisite privileges) is able to change the default mode; users, such as physicians, are not able to change the default mode. Clicking on button 1704 transfers the display to application store screen 1710, where a user can review and select various available applications and plug-ins. In screen 1710, a header section 1711 shows the system identification and has a field in which a user can enter search terms for application ("app") store (e.g., Apple® App store) products. Additional search criteria are shown in section 1712, such as, for example, limitation to programs with certain types of approvals, or limitation to specific medical fields, such as lungs, ear-nose-throat, brain, etc. Section 1713 displays the results returned from a search in lines 1714*a-n* and selection check boxes 1715*a-n*. A user may check a box to add a product to an electronic "shopping cart". When the user has made all desired selections, he may then click on button 1716 to activate the purchase and initiate the download.

Figure 18:
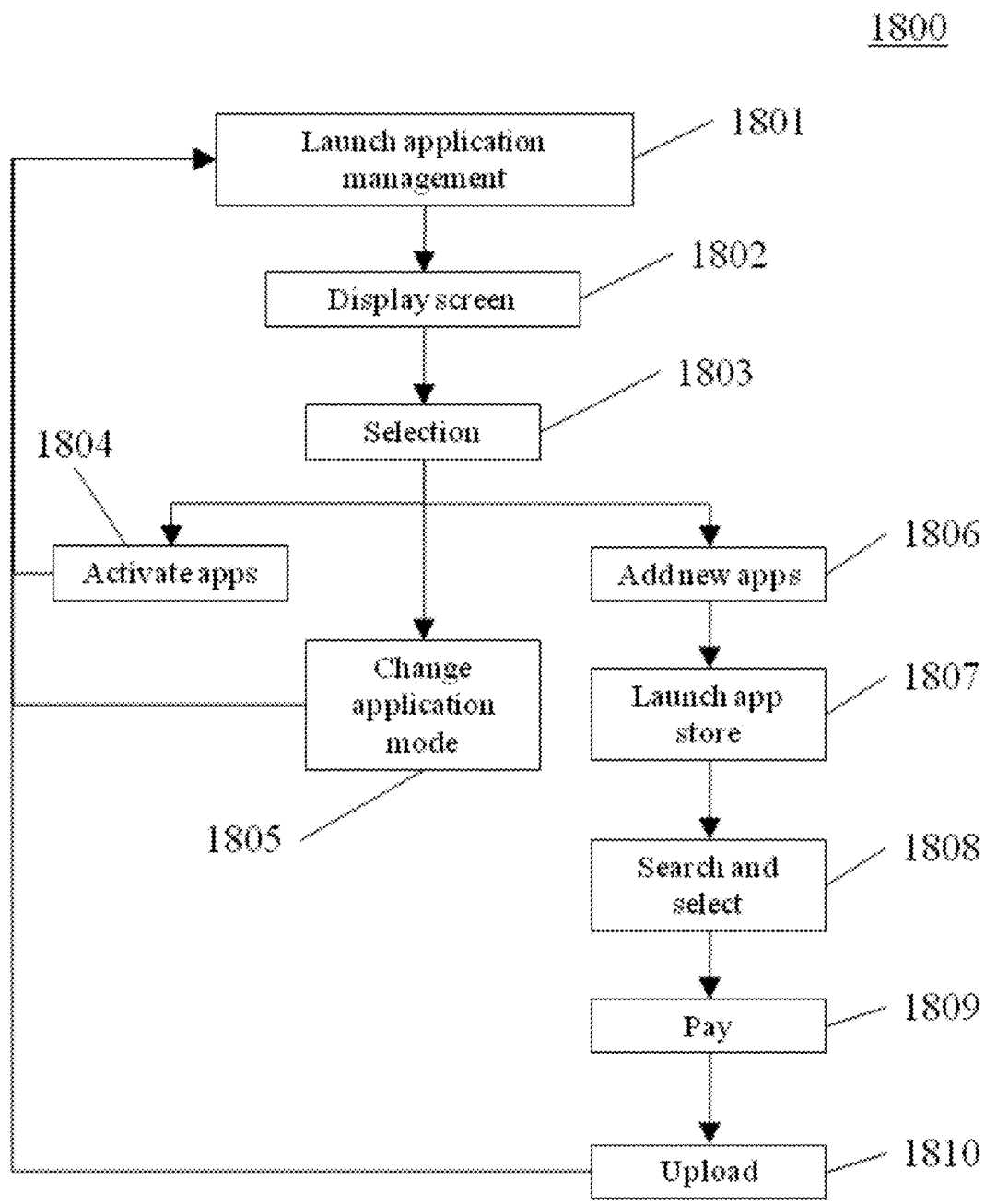
FIG. 18 shows an exemplary process for user interaction with app store modules.

FIG. 18 shows an exemplary process 1800 for user interaction with app store modules, in accordance with an embodiment of the invention. In step 1801, the application management module 1700 is launched. In step 1802, the screen is displayed and the user may begin the user's interaction with the system. In step 1803, the user makes a selection, after which one of various system modules may be launched. In selection 1804, the user has elected to activate certain previously inactive applications. If these applications include a non-approved application (e.g., a non-FDA approved application), an additional warning may appear on the screen, and then the mode, as shown, for example, in mode control area 1705, described above, may change to a non-approved mode. In selection 1805 the user may elect to change the application mode directly. This deliberate change of mode may result in certain applications becoming inactive if, for example, the user changes from a non-approved mode to an approved mode while certain non-approved applications are active. In selection 1806, the user has elected to add new apps to the system by clicking on button 1704, as described above. In step 1807, the system launches the app store 1710, and in step 1808 the user searches for apps that meet the user's specified criteria. The user then selects one or more products from the returned search results. In step 1809 payment is arranged, using any of various payment methods available for online stores, such as, for example, giving the system credit card information, or a billing arrangement with the system operator, or any other of many available payment options. In step 1810 the selected products are downloaded and installed. The selected products are then made available in application management screen 1800 for selection and activation.

Figure 19:
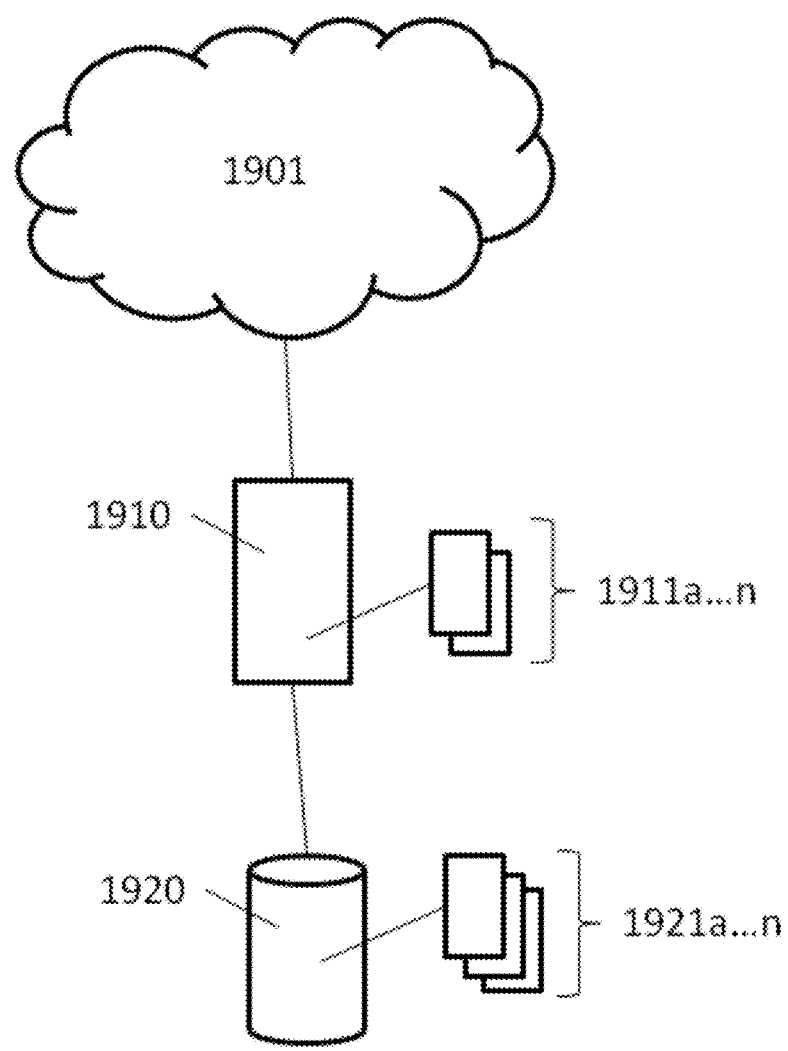
FIG. 19 shows an overview of an exemplary app store environment.

FIG. 19 shows an overview of an exemplary app store environment 1900, in accordance with an embodiment of the invention. The app store is connected to Internet 1901, which may be as described herein. Server 1910 has one or more software instances 1911*a-n*, including but not limited to operating system, web server, database, and other standard computer software, as well as the app store application, to be described in greater detail below. Storage unit 1920 contains various instances of data and software, including apps, plug-ins, and other merchandise 1921*a-n* for the store. In some cases, when server 1910 is not powered on, the storage unit 1920 includes software instances 1911*a-n*. Rather than a physical server 1910 and a physical storage unit 1920, the app store environment may comprise virtual machines and/or cloud services.

Figure 20:
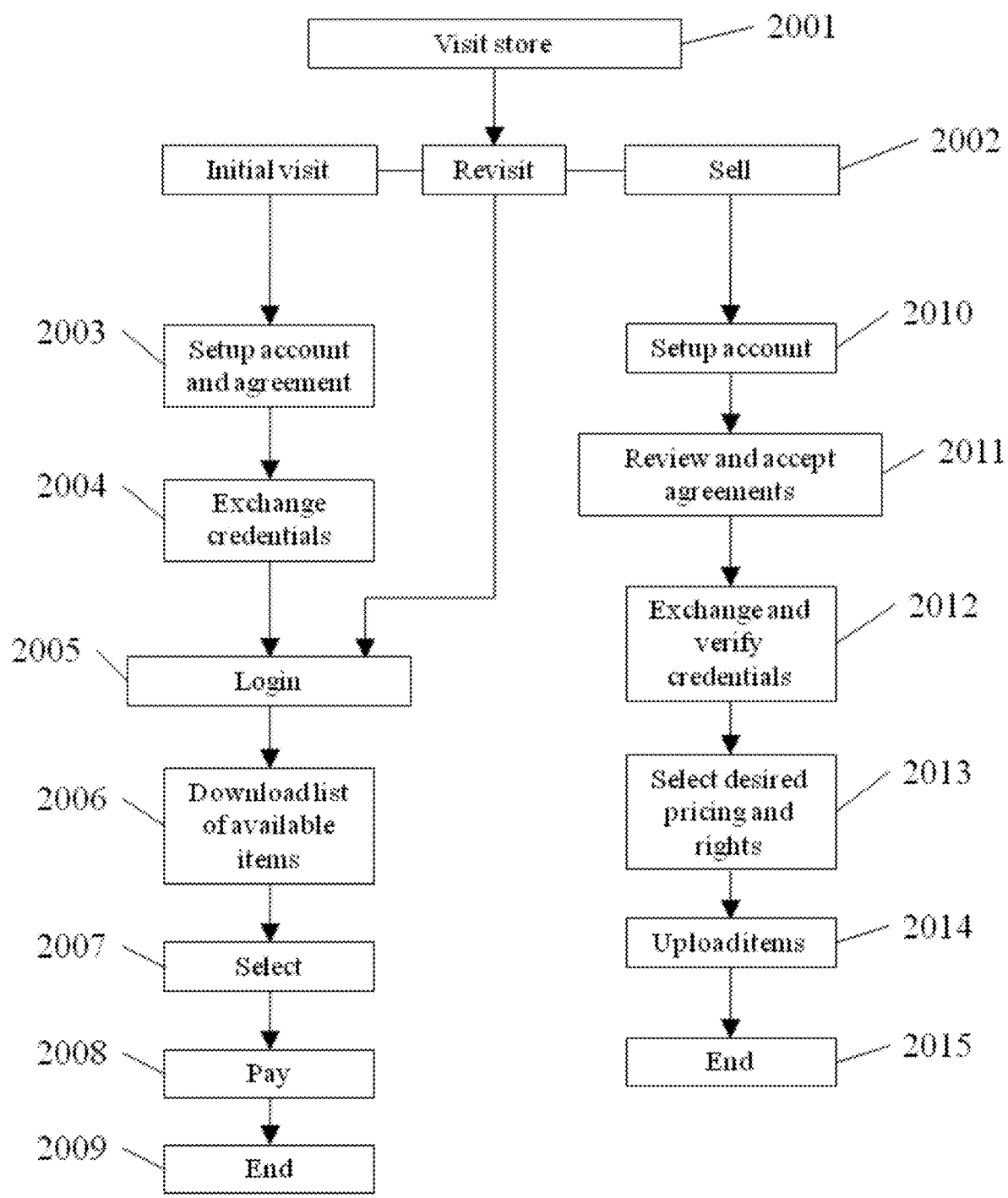
FIG. 20 shows an exemplary process for app store transactions.

FIG. 20 shows an exemplary process 2000 for app store transactions, in accordance with an embodiment of the invention. In step 2001, a user visits an app store. In step 2002, the user or the application selects the nature of the visit, such as a buyer's initial visit, a buyer's return visit, or a developer's visit to sell software. In some cases an application may interact directly, hiding the store, while in other cases, a web browser may be used, for example, for a developer to sell and upload software. If this is a buyer's initial visit, the process moves to step 2003, where the buyer sets up an account and is given the opportunity to review and accept one or more buying agreements, one or more of which agreements may specify one or more different types of regulatory approvals, as described below. In step 2004 the app store and the buyer's account exchange credentials to enable the store to verify the buyer's identity upon revisits. Upon the buyer's subsequent visit, the app store may require additional agreements to update, for example, verification of the buyer's identity or because of changes in the policies and merchandise of the store, changes in regulations governing the products and services, etc. In step 2005, the buyer, whether a first-time visitor or a return visitor, logs in with his verified credentials. In step 2006 the app store retrieves a list (e.g., by downloading the list) of available merchandise, and in step 2007 the user selects items from the list. Next, in step 2008 the buyer pays for his selected merchandise, using, for example, a built-in payment system, a third-party payment system, or some other available system for payment. In step 2009 the buyer downloads his merchandise and the transaction is finished.

At step 2002, if a buyer is revisiting the store, the system bypasses steps 2003 and 2004. The buyer is given the opportunity to login at step 2005.

In the case of a seller's visit to list merchandise for sale in the store, in step 2010 the seller sets up an account and in step 2011 the seller is given the opportunity to review and accept one or more agreements. When selling an item, a seller must decide what rights to give the buyer. For example, if a seller is selling a model, for example, of a typical disease appearance, or for boundary values, etc., rather than a software instance, the seller may give the buyer permission to use the model for the buyer's own purpose and/or within the buyer's organization, but in some cases the buyer does not have the right to distribute the model to any person or entity outside the buyer's organization unless he purchases some additional rights and licenses. In some cases, there may be additional restrictions associated with the buyer's permission to use the model. In some cases, the store may present a multi-level (with each level providing certain rights) agreement, and the seller may select the level of rights he is willing to sell. In step 2012, the store and the seller exchange and/or verify credentials. This exchange of credentials may be required upon each visit by a seller, even repeat visits, because each new instance of merchandise may require approval by a regulatory body (e.g., the FDA), and in such cases the seller is responsible for obtaining the required approvals. In some situations, credentials that verify the seller's machine may not be adequate; rather, the actual personal identity of the seller who vouches for regulatory compliance must be verified. In step 2013 the seller selects the desired pricing and rights for this particular merchandise from a multi-level agreement, as described above, or the seller may request additional pricing and rights agreements. In step 2014 the seller (or a computer system of or associated with the seller) uploads the seller's merchandise, and in step 2015 the transaction ends. The seller may receive payments for the merchandise by any payment system, which could be a proprietary payment system or a public system, such as credit card account, PayPal®, wire transfer, or credits (e.g., store credits).

Various modifications and variations of systems and methods disclosed herein may be made by one skilled in the art without departing from the spirit of the invention. For example, the system may retrieve one or more medical diagnostic images from an image database and use algorithms and rules to determine whether any of the images are of medical interest to a reviewing physician, and use tables to determine whether any one image should be part of a set of images. The system may then send the set of images to a display and analysis system for review by a physician or other qualified reviewer, who may, after reviewing the images, update the tables. Further, the system may track a patient's outcome by continuously following the initial findings and the responsiveness to treatment, and updating the tables accordingly. Additionally, the system may track the patient's clinical diagnosis and compare that with the initial radiological findings and then follow up in clinical treatment up to full resolution of the problem to determine whether the initial findings were supported or not, and if not, assessing any discrepancies and subsequently updating the tables with the discrepancy-related information or missing information, if any. Also, in tracking patient outcome, the diagnostics can be further enhanced and refined over time, thus improving the results by using machine learning at two levels, the first level involving looking at a final report by a radiologist and comparing it to the system's preliminary report, which may be automatically generated, and the second level involving adjusting/refining algorithms to match (or conform to) the radiologist's report.

For example, systems (e.g., PACS system, PAPVR system) and methods described herein may retrieve patient medical diagnostic images from an image database and then compare the current data to historical data of the patient. Further, based on the history of the patient and comparable data, the system may use preimposed historical data from the patient to further enhance analytics. The system may then compare initial findings to outcomes recorded in historical data, and make that additional finding available to a physician. Also, the system may use its findings to further improve analytics for future cases, using smart or targeted filtering that uses various methods described herein to detect various medical situations. Additionally, the diagnostic system may be used to identify specific attributes in the current case and then use those attributes to search a depository of medical data so that similar cases can be obtained to help a radiologist diagnose the current case. The system may provide relevant medical articles on the diagnosed disease or condition, and it may extracts time-dependent attributes (such as comparisons of two or more time points, e.g., clinical measurements, such as volume of pneumothorax). All such data may be made available to an operator; such available data may include, without limitation, volume, attributes, measurements, statistics, examples from similar cases, as well as relevant publications in a preliminary report for a radiologist to use in creating a final report to the referring physician.

In some embodiments, a method for providing medical diagnostics comprises providing access to one or more platforms ("platform") capable of distributing one or more applications configured to implement a method comprising retrieving, using a processor, one or more images from an image database or an imaging device, the one or more images defining a set of images; determining, using a processor, whether each of the images is of medical interest to a reviewing physician; providing one or more images to a display and analysis system for review by a reviewing physician, wherein the one or more images are provided with an image that is representative of the set of images. The platform may be a computer system having the processor among one or a plurality of processors.

In an embodiment, the platform receives a selection by a user for one or more of the applications accessible by the platform, and provides the one or more selected applications to the user. In another embodiment, the platform receives one or more search parameters from the user and provides the user an option for one or more applications that meet the one or more search parameters. The user may elect the option provided by the computer system. The one or more selected applications, in some cases, are provided to the user on a per use or subscription model (or basis).

The platform may permit one or more developers to download or purchase one or more APIs and/or SDKs. In some cases, the platform may provide a test mode capable of receiving a clinical data set to test one or more selected application. In some cases, if the test is successful, a protocol is provided to submit and clear the application. In some situations, the platform indicates whether the one or more applications are FDA approved, are in process for FDA approval, or have another status.

In some embodiments, a system for providing medical diagnostics comprises one or more platforms ("platform") capable of distributing one or more applications configured to implement a method comprising retrieving, using a processor, one or more images from an image database or an imaging device, the one or more images defining a set of images; determining, using a processor, whether each of the images is of medical interest to a reviewing physician; and providing one or more images to a display and analysis system for review by a reviewing physician, wherein the one or more images are provided with an image that is representative of the set of images. The system further comprises an interface, such as a graphical user interface (GUI), configured to receive one or more user input related to the distribution of the one or more applications.

In some cases, a platform for evaluating and distributing apps to provide enhanced analytics, alerts, notifications, etc., through an app store may be made available, where customers can search for applications ("apps") of interest and buy selected apps on a per-use, one-time license fee, or subscription model. Further, for third-party developers, the platform may provide an application programming interface (API), software development kit (SDK), and test mode in which it provides clinical data to test the app, and if successful, provides a protocol to submit and clear the app through a regulatory body (e.g., FDA), if required. In addition, the app store may have a categorization and a smart filtering system to enable customers to view the statuses (e.g., approved, denied) of applications and, in some cases, view approved applications, and review informal ideas shared by other professionals without requiring the user to do manual verification. For example, the app store shows customers whether an app is FDA approved, in process, or not in process.

Systems and methods of the disclosure may be combined with or modified by other systems and methods, such as those described in PCT/US2011/023059 ("METHODS AND SYSTEMS FOR ANALYZING, PRIORITIZING, VISUALIZING, AND REPORTING MEDICAL IMAGES"), which is entirely incorporated herein by reference.

These modifications and variations do not depart from its broader spirit and scope, and the examples cited here are to be regarded in an illustrative rather than a restrictive sense.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A method comprising:

retrieving, by a computer system, scan data of a predetermined region of a patient's body, the scan data comprising at least one image of the predetermined region;

automatically analyzing, using the computer system, the scan data to identify an abnormality relating to the patient's condition using an image processing algorithm;

automatically performing, using the computer system, quantitative measurements relating to the abnormality using image analysis, wherein the quantitative measurements are associated with at least one of a distance, a cross-sectional area, and a volume relating to the patient's condition;

automatically identifying, using the computer system, a representative image from the scan data based on the identified abnormality and the quantitative measurements relating to the abnormality;

automatically generating, using the computer system, an analysis report including at least one of the representative image and the quantitative measurements associated with the representative image;

retrieving, using the computer system, a historical analysis report of the predetermined region of the patient's body, wherein the historical analysis report includes at least one of a historical representative image and quantitative measurements associated with the historical representative image;

automatically comparing, using the computer system, the quantitative measurements relating to the abnormality in the analysis report with the quantitative measurements relating to the abnormality in the historical analysis report to identify a change in the patient's condition;

determining, using a machine learning model, a change in diagnosis associated with the patient based at least in part on the identified change in the patient's condition, the change in diagnosis being indicative of a potential problem in a historical diagnosis or a progression of the patient's condition, wherein the machine learning model was generated by:

receiving a plurality of final reports associated with the physician and a corresponding plurality of preliminary reports generated by an initial machine learning model;

comparing the plurality of final reports by the physician with the corresponding plurality of preliminary reports to adjust the initial machine learning model to more closely match the plurality of final reports; and further refining the initial machine learning model based at least in part on patient outcome information relating to patient responsiveness to treatment, the treatment being associated with conditions identified in the plurality of preliminary reports generated by the initial machine learning model; and presenting, using the computer system, a preliminary report associated with the change in diagnosis to a physician for review, wherein the preliminary report associated with the change in diagnosis includes at least one of (i) the representative image and historical representative image, (ii) the quantitative measurements relating to the abnormality in the analysis report and the quantitative measurements relating to the abnormality in the historical analysis report, and (iii) the change in diagnosis determined by the machine learning model.

2. The method of claim 1, wherein the abnormality is determined using comparable images or severity range lookup tables based on the patient's condition.

3. The method of claim 1, further comprising retrieving data from one or more additional information source.

4. The method of claim 3, wherein the one or more additional information source includes one or more of the following: news articles, or data from one or more additional patients.

5. The method of claim 4, wherein the additional information is included in the analysis report.

6. The method of claim 4, wherein the additional information is used to analyze the plurality of images associated with the patient.

7. The method of claim 6, further comprising detecting one or more medical conditions of the patient based on using the additional information to analyze the plurality of images associated with the patient.

8. The method of claim 4, wherein the one or more additional patients shares one or more peer group attribute with the patient.

9. The method of claim 1, further comprising providing an alert if parameters associated with the plurality of images fall within one or more boundary parameters, wherein the one or more boundary parameters associated with the plurality of images.

10. The method of claim 8, further comprising retrieving, from a memory location coupled to the processor, data sets associated with the one or more peer group attributes.

11. The method of claim 1, wherein the analysis report comprises diagnostic data.

12. The method of claim 11, wherein the diagnostic data comprises one or more of the following: volume, attributes, measurements, statistics, examples from one or more similar cases of an additional subject, and examples from one or more articles.

13. The method of claim 11, further comprising extracting one or more time-dependent attributes from the diagnostic data.

14. The method of claim 11, further comprising sorting the diagnostic data of the subject according to one or more of the following peer group attributes: age, gender, life style, habits, disease, and stage of disease.

15. The method of claim 11, wherein the diagnostic data comprises two or more of the following: volume, attributes, measurements, statistics, examples from one or more similar cases of an additional subject, and examples from one or more articles.

16. The method of claim 11, wherein the diagnostic data comprises three or more of the following: volume, attributes, measurements, statistics, examples from one or more similar cases of an additional subject, and examples from one or more articles.

17. The method of claim 1, wherein the plurality of images are from a first time point, and wherein the historical analysis report includes time-dependent attributes of one or more images of the patient from a second time point, wherein the second time point precedes the first time point.

18. The method of claim 17, further comprising comparing time-dependent attributes of the set of images of the first time point with historical data and quantifying changes in time-dependent attributes between the first time point and the second time point.

19. The method of claim 18, further comprising generating information on the quantified changes in time-dependent attributes between the first time point and the second time point of at least one image of the set of images, wherein the quantified changes enable tracking a medical progress of said subject.

20. The method of claim 1, further comprising designating an image priority, wherein the image priority is based on comparing each of the plurality of images to the plurality of images.

21. The method of claim 20, wherein the designating an image priority is further based on at least one of additional information and the historical analysis report.

22. The method of claim 20, wherein the image priority includes a designation of high, medium, or low priority.

23. The method of claim 20, wherein the image priority includes a designation of a non-negative integer, wherein higher priority images are assigned a lower numerical value.

24. The method of claim 22, further comprising prioritizing the plurality of images.

25. The method of claim 23, further comprising prioritizing the plurality of images.

26. The method of claim 1, further comprising designating a case priority, wherein the case priority is designated based on the patient's condition.

27. The method of claim 26, wherein the case priority includes a designation of a high, medium, or low priority.

28. The method of claim 26, further comprising prioritizing a plurality of cases.

29. The method of claim 1, wherein the patient's condition comprises pneumothorax, and wherein the quantitative measurements are associated with at least the volume relating to the patient's condition and comprise quantifying a volume of air or a liquid pocket.

30. The method of claim 1, wherein the patient's condition comprises pleural effusion, and wherein the quantitative measurements are associated with at least the volume relating to the patient's condition and comprise quantifying a volume of free liquid and free air in a pleural cavity.

31. The method of claim 1, wherein the patient's condition comprises an aortic dissection, and wherein the quantitative measurements are associated with at least the cross-sectional area relating to the patient's condition and comprise quantifying a cross-sectional dimension of an aorta.

32. The method of claim 1, wherein the patient's condition comprises a fracture, and wherein the quantitative measurements comprise quantifying a dimension of the fracture.

33. The method of claim 1, wherein the patient's condition comprises an intracranial hemorrhage.

34. The method of claim 1, wherein the patient's condition comprises a liver metastasis.

35. The method of claim 1, wherein the patient's condition comprises an aortic aneurysm, and wherein the quantitative measurements comprise quantifying dilation of an aorta.

36. The method of claim 1, further comprising generating an indication of localization of the abnormality in the representative image.

37. The method of claim 36, wherein the analysis report further includes the indication of localization of the abnormality.

38. The method of claim 37, wherein the comparison report further includes the indication of localization of the abnormality.

39. The method of claim 1, further comprising:
   receiving a final report from the physician after the presenting the preliminary report;
   comparing the final report with the preliminary report; and
   further refining the machine learning model based at least in part on the comparison.

* * * * *